United States Patent
Heaney et al.

(10) Patent No.: US 11,464,575 B2
(45) Date of Patent: Oct. 11, 2022

(54) SYSTEMS, METHODS, APPARATUSES, AND COMPUTER-READABLE MEDIA FOR IMAGE GUIDED SURGERY

(71) Applicant: InnerOptic Technology, Inc., Hillsborough, NC (US)

(72) Inventors: Brian Heaney, Durham, NC (US); John Martinie, Charlotte, NC (US); David Iannitti, Charlotte, NC (US); Andrei State, Chapel Hill, NC (US); Sharif Razzaque, Boulder, CO (US)

(73) Assignee: InnerOptic Technology, Inc., Hillsborough, NC (US)

( * ) Notice: Subject to any disclaimer, the term of this patent is extended or adjusted under 35 U.S.C. 154(b) by 642 days.

(21) Appl. No.: 16/178,002

(22) Filed: Nov. 1, 2018

(65) Prior Publication Data

US 2019/0167354 A1  Jun. 6, 2019

Related U.S. Application Data

(63) Continuation of application No. 15/182,346, filed on Jun. 14, 2016, now Pat. No. 10,136,951, which is a
(Continued)

(51) Int. Cl.
*A61B 34/20* (2016.01)
*A61B 18/14* (2006.01)
(Continued)

(52) U.S. Cl.
CPC ............ *A61B 34/20* (2016.02); *A61B 8/4245* (2013.01); *A61B 18/1477* (2013.01);
(Continued)

(58) Field of Classification Search
CPC ......... A61B 34/20; A61B 34/10; A61B 34/25; A61B 90/37; A61B 18/1815;
(Continued)

(56) References Cited

U.S. PATENT DOCUMENTS 3,556,079 A 1/1971 Omizo
4,058,114 A 11/1977 Soldner
(Continued)

FOREIGN PATENT DOCUMENTS

AU 7656896 A 5/1997
AU 9453898 A 4/1999
(Continued)

OTHER PUBLICATIONS

U.S. Appl. No. 11/828,826 including its ongoing prosecution history, including without limitation Office Actions, Amendments, Remarks, and any other potentially relevant documents, filed Jul. 26, 2007, Keller et al.
(Continued)

*Primary Examiner* — Peter Luong
(74) *Attorney, Agent, or Firm* — Knobbe Martens Olson & Bear LLP

(57) ABSTRACT

Presented herein are methods, systems, devices, and computer-readable media for image guided surgery. The systems herein allow a physician to use multiple instruments for a surgery and simultaneously provide image-guidance data for those instruments. Various embodiments disclosed herein provide information to physicians about procedures they are performing, the devices (such as ablation needles, ultrasound wands or probes, scalpels, cauterizers, etc.) they are using during the procedure, the relative emplacements or poses of these devices, prediction information for those devices, and other information. Some embodiments provide useful information about 3D data sets. Additionally, some embodiments provide for quickly calibratable surgical instruments or attachments for surgical instruments.

18 Claims, 23 Drawing Sheets

Related U.S. Application Data continuation of application No. 14/166,173, filed on Jan. 28, 2014, now Pat. No. 9,398,936, which is a continuation of application No. 12/703,118, filed on Feb. 9, 2010, now Pat. No. 8,690,776.

(60) Provisional application No. 61/207,589, filed on Feb. 17, 2009, provisional application No. 61/207,593, filed on Feb. 17, 2009, provisional application No. 61/207,592, filed on Feb. 17, 2009.

(51) Int. Cl.

| | | |
|---|---|---|
| *A61B 8/00* | (2006.01) | |
| *A61B 34/00* | (2016.01) | |
| *A61B 34/10* | (2016.01) | |
| *A61B 90/00* | (2016.01) | |
| *A61B 18/18* | (2006.01) | |
| *B33Y 80/00* | (2015.01) | |
| *A61B 18/02* | (2006.01) | |
| *A61B 18/08* | (2006.01) | |
| *A61B 18/20* | (2006.01) | |
| *A61B 90/50* | (2016.01) | |
| *A61B 18/00* | (2006.01) | |

(52) U.S. Cl.
CPC .......... *A61B 18/1815* (2013.01); *A61B 34/10* (2016.02); *A61B 34/25* (2016.02); *A61B 90/37* (2016.02); *A61B 18/02* (2013.01); *A61B 18/082* (2013.01); *A61B 18/1442* (2013.01); *A61B 18/18* (2013.01); *A61B 18/20* (2013.01); *A61B 2018/00577* (2013.01); *A61B 2018/1425* (2013.01); *A61B 2018/1869* (2013.01); *A61B 2034/102* (2016.02); *A61B 2034/104* (2016.02); *A61B 2034/107* (2016.02); *A61B 2034/207* (2016.02); *A61B 2034/2051* (2016.02); *A61B 2034/2072* (2016.02); *A61B 2090/368* (2016.02); *A61B 2090/378* (2016.02); *A61B 2090/3983* (2016.02); *A61B 2090/502* (2016.02); *B33Y 80/00* (2014.12)

(58) Field of Classification Search
CPC ... A61B 18/1477; A61B 18/02; A61B 18/082; A61B 18/1442; A61B 18/18; A61B 18/20; A61B 8/4245; A61B 2018/00577; A61B 2018/1869; A61B 2018/1425; A61B 2090/378; A61B 2090/3983; A61B 2090/502; A61B 2090/368; A61B 2034/107; A61B 2034/2051; A61B 2034/102; A61B 2034/10; A61B 2034/207; A61B 2034/2072; B33Y 80/00
See application file for complete search history.

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,158,088 A | 10/1992 | Nelson et al. |
| 5,161,536 A | 11/1992 | Vikomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli et al. |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,806,521 A | 9/1998 | Morimoto et al. |
| 5,807,395 A | 9/1998 | Mulier et al. |

(56) References Cited

U.S. PATENT DOCUMENTS

| | | |
|---|---|---|
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bodiolz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,967,991 A | 10/1999 | Gardineer et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,784 B1 | 6/2001 | Summers et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olsdat |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Bjaerum et al. |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Oltad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,596,267 B2 | 9/2009 | Accomazzi et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,747,305 B2 | 6/2010 | Dean et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |

(56) References Cited

U.S. PATENT DOCUMENTS

| | | |
|---|---|---|
| 8,350,902 B2 | 1/2013 | Razzaque et al. |
| 8,482,606 B2 | 7/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 9,107,698 B2 | 8/2015 | Razzaque et al. |
| 9,265,572 B2 | 2/2016 | Fuchs et al. |
| 9,282,947 B2 | 3/2016 | Razzaque et al. |
| 9,364,294 B2 | 6/2016 | Razzaque et al. |
| 9,398,936 B2 | 7/2016 | Razzaque et al. |
| 9,659,345 B2 | 5/2017 | Razzaque et al. |
| 9,675,319 B1 | 6/2017 | Razzaque et al. |
| 9,901,406 B2 | 2/2018 | State et al. |
| 9,949,700 B2 | 4/2018 | Razzaque et al. |
| 10,026,191 B2 | 7/2018 | Accomando et al. |
| 10,127,629 B2 | 11/2018 | Razzaque et al. |
| 10,136,951 B2 | 11/2018 | Razzaque et al. |
| 10,188,467 B2 | 1/2019 | Razzaque et al. |
| 10,278,778 B2 | 5/2019 | State et al. |
| 10,314,559 B2 | 6/2019 | Razzaque et al. |
| 10,398,513 B2 | 9/2019 | Razzaque et al. |
| 10,433,814 B2 | 10/2019 | Razzaque et al. |
| 10,733,700 B2 | 8/2020 | Keller et al. |
| 10,772,686 B2 | 9/2020 | State et al. |
| 10,820,944 B2 | 11/2020 | State et al. |
| 10,820,946 B2 | 11/2020 | Heaney et al. |
| 2001/0007919 A1 | 7/2001 | Shahidi |
| 2001/0016804 A1 | 8/2001 | Cunningham et al. |
| 2001/0031920 A1 | 10/2001 | Kaufman et al. |
| 2001/0041838 A1 | 11/2001 | Holupka et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzle, III |
| 2002/0077543 A1 | 6/2002 | Grzeszczuk et al. |
| 2002/0103431 A1 | 8/2002 | Toker et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0032878 A1 | 2/2003 | Shahidi |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2003/0233123 A1 | 12/2003 | Kindlein et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0033160 A1* | 2/2005 | Yamagata ............ A61B 6/12 600/425 |
| 2005/0085717 A1 | 4/2005 | Shahidi |
| 2005/0085718 A1 | 4/2005 | Shahidi |
| 2005/0090733 A1 | 4/2005 | Van Der Lugt et al. |
| 2005/0090742 A1 | 4/2005 | Mine et al. |
| 2005/0107679 A1 | 5/2005 | Geiger et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0231532 A1 | 10/2005 | Suzuki et al. |
| 2005/0240094 A1 | 10/2005 | Pichon et al. |
| 2005/0251148 A1 | 11/2005 | Friedrich |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0004275 A1 | 6/2006 | Vija et al. |
| 2006/0122495 A1 | 6/2006 | Kienzle |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0002582 A1 | 1/2007 | Burwell et al. |
| 2007/0016035 A1 | 1/2007 | Hashimoto |
| 2007/0024617 A1 | 2/2007 | Poole |
| 2007/0032906 A1 | 2/2007 | Sutherland et al. |
| 2007/0073155 A1 | 3/2007 | Park et al. |
| 2007/0073455 A1 | 3/2007 | Oyobe et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kristofferson et al. |
| 2007/0270718 A1 | 11/2007 | Rochetin et al. |
| 2007/0276234 A1 | 11/2007 | Shahidi |
| 2007/0291000 A1 | 12/2007 | Liang et al. |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0146939 A1 | 6/2008 | McMorrow et al. |
| 2008/0161824 A1 | 7/2008 | McMillen |
| 2008/0183080 A1 | 7/2008 | Abraham |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0036902 A1 | 2/2009 | DeMaio et al. |
| 2009/0105597 A1 | 4/2009 | Abraham |
| 2009/0118613 A1 | 5/2009 | Krugman et al. |
| 2009/0118724 A1 | 5/2009 | Zvuloni et al. |
| 2009/0131783 A1 | 5/2009 | Jenkins et al. |
| 2009/0137907 A1* | 5/2009 | Takimoto ............ A61B 8/466 600/461 |
| 2009/0196480 A1 | 8/2009 | Nields et al. |
| 2009/0234369 A1 | 9/2009 | Bax et al. |
| 2009/0312629 A1 | 12/2009 | Razzaque et al. |
| 2010/0045783 A1 | 2/2010 | State et al. |

(56) References Cited

U.S. PATENT DOCUMENTS

| | | |
|---|---|---|
| 2010/0152570 A1 | 6/2010 | Navab |
| 2010/0185087 A1 | 7/2010 | Nields et al. |
| 2010/0198045 A1 | 8/2010 | Razzaque et al. |
| 2010/0198402 A1 | 8/2010 | Greer et al. |
| 2010/0208963 A1 | 8/2010 | Kruecker et al. |
| 2010/0268072 A1 | 10/2010 | Hall et al. |
| 2010/0268085 A1 | 10/2010 | Kruecker et al. |
| 2010/0296718 A1 | 11/2010 | Ostrovsky-Berman et al. |
| 2010/0298705 A1 | 11/2010 | Pelissier et al. |
| 2010/0305448 A1 | 12/2010 | Dagonnau et al. |
| 2010/0312121 A1 | 12/2010 | Guan |
| 2010/0331252 A1 | 12/2010 | Hamrick |
| 2011/0043612 A1 | 2/2011 | Keller et al. |
| 2011/0046483 A1 | 2/2011 | Fuchs et al. |
| 2011/0046486 A1 | 2/2011 | Shin et al. |
| 2011/0057930 A1 | 3/2011 | Keller |
| 2011/0082351 A1 | 4/2011 | Razzaque et al. |
| 2011/0201915 A1 | 8/2011 | Gogin et al. |
| 2011/0201976 A1 | 8/2011 | Sanghvi et al. |
| 2011/0208055 A1 | 8/2011 | Dalal et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0108955 A1 | 5/2012 | Razzaque et al. |
| 2012/0138658 A1 | 6/2012 | Ullrich et al. |
| 2012/0143029 A1 | 6/2012 | Silverstein et al. |
| 2012/0143055 A1 | 6/2012 | Ng et al. |
| 2012/0165679 A1 | 6/2012 | Orome et al. |
| 2012/0215096 A1 | 8/2012 | Gilboa |
| 2012/0230559 A1 | 9/2012 | Itai |
| 2012/0237105 A1 | 9/2012 | Mielekamp |
| 2012/0259210 A1 | 10/2012 | Harhen et al. |
| 2013/0030286 A1 | 1/2013 | Alouani et al. |
| 2013/0044930 A1 | 2/2013 | Li et al. |
| 2013/0079770 A1 | 3/2013 | Kyle, Jr. et al. |
| 2013/0090646 A1 | 4/2013 | Moss et al. |
| 2013/0096497 A1 | 4/2013 | Duindam et al. |
| 2013/0132374 A1 | 5/2013 | Olstad et al. |
| 2013/0144165 A1 | 6/2013 | Ebbini et al. |
| 2013/0151533 A1 | 6/2013 | Udupa et al. |
| 2013/0178745 A1 | 7/2013 | Kyle et al. |
| 2013/0218024 A1 | 8/2013 | Boctor et al. |
| 2013/0249787 A1 | 9/2013 | Morimoto |
| 2014/0051987 A1 | 2/2014 | Kowshik et al. |
| 2014/0058387 A1 | 2/2014 | Kruecker et al. |
| 2014/0078138 A1 | 3/2014 | Martin et al. |
| 2014/0180074 A1 | 6/2014 | Green |
| 2014/0201669 A1 | 7/2014 | Liu et al. |
| 2014/0275760 A1 | 9/2014 | Lee et al. |
| 2014/0275810 A1 | 9/2014 | Keller et al. |
| 2014/0275997 A1 | 9/2014 | Chopra et al. |
| 2014/0343404 A1 | 11/2014 | Razzaque et al. |
| 2014/0350390 A1 | 11/2014 | Kudavelly et al. |
| 2015/0238259 A1 | 8/2015 | Albeck et al. |
| 2015/0257847 A1 | 9/2015 | Higgins et al. |
| 2016/0117857 A1 | 4/2016 | State et al. |
| 2016/0166334 A1 | 6/2016 | Razzaque |
| 2016/0166336 A1 | 6/2016 | Razzaque |
| 2016/0196694 A1 | 7/2016 | Lindeman |
| 2016/0270862 A1 | 9/2016 | Fuchs et al. |
| 2016/0354152 A1 | 12/2016 | Beck |
| 2017/0024903 A1 | 1/2017 | Razzaque |
| 2017/0065352 A1 | 3/2017 | Razzaque |
| 2017/0099479 A1 | 4/2017 | Browd et al. |
| 2017/0128139 A1 | 5/2017 | Razzaque et al. |
| 2017/0323424 A1 | 11/2017 | Razzaque et al. |
| 2017/0348067 A1 | 12/2017 | Krimsky |
| 2017/0360395 A1 | 12/2017 | Razzaque et al. |
| 2018/0116731 A1 | 5/2018 | State et al. |
| 2018/0263713 A1 | 9/2018 | State |
| 2018/0289344 A1 | 10/2018 | Green et al. |
| 2019/0021681 A1 | 1/2019 | Kohli |
| 2019/0060001 A1 | 2/2019 | Kohli et al. |
| 2019/0223958 A1 | 7/2019 | Kohli |
| 2019/0247130 A1 | 8/2019 | State |
| 2020/0046315 A1 | 2/2020 | State |
| 2020/0138402 A1 | 5/2020 | Kohli |
| 2021/0027418 A1 | 1/2021 | Keller |
| 2021/0113273 A1 | 4/2021 | State |
| 2021/0161600 A1 | 6/2021 | Heaney |
| 2021/0161601 A1 | 6/2021 | State |

FOREIGN PATENT DOCUMENTS

| | | |
|---|---|---|
| AU | 1719601 A | 6/2001 |
| AU | 9036301 A | 3/2002 |
| AU | 2003297225 A1 | 7/2004 |
| AU | 2001290363 B2 | 2/2006 |
| BR | 0113882 A | 7/2003 |
| CA | 2420382 C | 4/2011 |
| DE | 60126798 T2 | 10/2007 |
| EP | 0 427 358 | 5/1991 |
| EP | 1955284 | 8/2008 |
| JP | S63-290550 A | 11/1988 |
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/005768 | 2/1996 |
| WO | WO 97/015249 | 5/1997 |
| WO | WO 97/017014 | 5/1997 |
| WO | WO 97/029682 | 8/1997 |
| WO | WO 99/26534 | 6/1999 |
| WO | WO 01/039683 | 6/2001 |
| WO | WO 03/032837 | 4/2003 |
| WO | WO 03/034705 | 4/2003 |
| WO | WO 03/105289 | 12/2003 |
| WO | WO 05/010711 | 2/2005 |
| WO | WO 07/019216 | 2/2007 |
| WO | WO 07/067323 A2 | 6/2007 |
| WO | WO 07/067323 A3 | 9/2007 |
| WO | WO 08/017051 A2 | 2/2008 |
| WO | WO 09/063423 | 5/2009 |
| WO | WO 09/094646 | 7/2009 |
| WO | WO 10/057315 | 5/2010 |
| WO | WO 10/096419 A2 | 8/2010 |
| WO | WO 11/014687 A2 | 2/2011 |
| WO | WO 12/169990 | 12/2012 |
| WO | WO 18/080844 | 5/2018 |

OTHER PUBLICATIONS

U.S. Appl. No. 15/041,868 including its ongoing prosecution history, including without limitation Office Actions, Amendments, Remarks, and any other potentially relevant documents, filed Feb. 11, 2016, Fuchs et al.

U.S. Appl. No. 15/068,323 including its ongoing prosecution history, including without limitation Office Actions, Amendments, Remarks, and any other potentially relevant documents, filed Mar. 11, 2016, Razzaque et al.

U.S. Appl. No. 15/199,630 including its ongoing prosecution history, including without limitation Office Actions, Amendments, Remarks, and any other potentially relevant documents Iss'd now U.S. Pat. No. 9,675,319 on Jun. 13, 2017, filed Jun. 30, 2016, Razzaque et al.

U.S. Appl. No. 15/415,398 including its ongoing prosecution history, including without limitation Office Actions, Amendments, Remarks, and any other potentially relevant documents, filed Jan. 25, 2017, State et al.

U.S. Appl. No. 15/598,616 including its ongoing prosecution history, including without limitation Office Actions, Amendments,

(56) References Cited

OTHER PUBLICATIONS

Remarks, and any other potentially relevant documents Pub'd 2017/0323424, filed May 18, 2017, Razzaque et al.
U.S. Appl. No. 15/799,639 including its ongoing prosecution history, including without limitation Office Actions, Amendments, Remarks, and any other potentially relevant documents, filed Oct. 31, 2017, Green et al.
U.S. Appl. No. 15/882,709 including its ongoing prosecution history, including without limitation Office Actions, Amendments, Remarks, and any other potentially relevant documents, filed Jan. 29, 2018, State et al.
U.S. Appl. No. 15/995,059 including its ongoing prosecution history, including without limitation Office Actions, Amendments, Remarks, and any other potentially relevant documents, filed Apr. 17, 2018, Kohli et al.
U.S. Appl. No. 16/052,289 including its ongoing prosecution history, including without limitation Office Actions, Amendments, Remarks, and any other potentially relevant documents, filed Aug. 1, 2018, Kohli et al.
U.S. Appl. No. 16/177,894 including its ongoing prosecution history, including without limitation Office Actions, Amendments, Remarks, and any other potentially relevant documents, filed Nov. 1, 2018, Keller et al.
"3D Laparoscope Technology," http://www.inneroptic.com/tech_3DL.htm, copyright 2007 InnerOptic Technology, Inc. printed Sep. 19, 2007, 2 pages.
"Cancer Facts & Figures 2004," www.cancer.org/downloads/STT/CAFF_finalPWSecured.pdf, copyright 2004 American Cancer Society, Inc., printed Sep. 19, 2007, 60 pages.
Cancer Prevention & Early Detection Facts & Figures 2004; National Center for Tobacco-Free Kids; 2004; American Cancer Society; USA.
"David Laserscanner <-Latest News <- Institute for Robotics and Process Control <- Te . . . ," http://www/rob.cs.tu-bs.de/en/news/david, printed Sep. 19, 2007, 1 page.
"Laser scanned 3d model Final" video, still image of video attached, http://www.youtube.com/watch?v=DaLglgmoUf8, copyright 2007 YouTube, LLC, printed Sep. 19, 2007, 2 pages.
"Olympus Endoscopic Ultrasound System," www.olympusamerica.com/msg_section/download_brochures/135_b_gfum130.pdf, printed Sep. 20, 2007, 20 pages.
"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.
"Robbins, Mike—Computer Vision Research—Stereo Depth Perception," http://www.compumike.com/vision/stereodepth. php, copyright 2007 Michael F. Robbins, printed Sep. 19, 2007, 3 pages.
"Rue, Registered Ultrasound-Endoscope," copyright 2007 InnerOptic Technology, Inc., 2 pages.
Advertisement, "Inspeck 3DC 3D Capturor," Inspeck 3DC 3D Capturor (www.inspeck.com), 1998.
Advertisement, "Virtual 3D High Speed Non-Contact Surface Perception," Virtual 3-D Technologies Corporation (www.virtual3dtech.com)., Dec. 21, 1998.
Advertisements, "Virtuoso," Visual Interface, Inc. (www.visint.com), Dec. 21, 1998.
Akka, "Automatic Software Control of Display Parameters for Stereoscopic Graphics Images," SPIE vol. 1669: Stereoscopic Displays and Applications III, pp. 31-38 (1992).
Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.
Aylward et al., Analysis of the Parameter Space of a Metric for Registering 3D Vascular Images, in W. Niessen and M. Viergever (Eds.): MICCAI 2001, LNCS 2208, pp. 932-939, 2001.
Aylward et al., Registration and Analysis of Vascular Images, International Journal of Computer Vision 55(2/3), 123-138, 2003.
Aylward, et al., Intra-Operative 3D Ultrasound Augmentation, Proceedings of the IEEE International Symposium on Biomedical Imaging, Washington, Jul. 2002.
Azuma et al., "Improving Static and Dynamic Registration in an Optical See-Through HMD," Paper Presented at SIGGRAPH '94 Annual Conference in Orlando, FL, 17 pages (1994).
Azuma, "A Survey of Augmented Reality," Presence: Teleoperators and Virtual Environments 6, 4:1-48 (Aug. 1997).
Badler et al., "Simulating Humans: Computer Graphics, Animation, and Control," Oxford University Press (1993).
Bajura, Michael et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.
Benavides et al., "Multispectral digital colposcopy for in vivo detection of cervical cancer," Optics Express; May 19, 2003; 11(10) Optical Society of America; USA.
Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.
Billinghurst, M. et al., Research Directions in Handheld AR; Int. J. of Virtual Reality 5(2),51-58 (2006).
Blais, F., "Review of 20 Years of Range Sensor Development," Journal of Electronic Imaging, 13(1):231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.
Bouguet, Jean-Yves, "Camera Calibration Toolbox for Matlab," www.vision.caltech.edu/bouguetj/calib_doc, printed Sep. 20, 2007, 5 pages.
Buxton et al.; "Colposcopically directed punch biopsy: a potentially misleading investigation," British Journal of Obstetrics and Gynecology; Dec. 1991 ; 98:1273-1276.
Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.
Cantor et al., "Cost-Effectiveness Analysis of Diagnosis and Management of Cervical Squamous Intraepithelial Lesions," Diagnostic Strategies for SILs; Feb. 1998; 91(2):270-277.
Catalano et al. "Multiphase helical CT findings after percutaneous ablation procedures for hepatocellular carcinoma." Abdom. Imaging, 25(6),2000, pp. 607-614.
Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.
Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.
Deering, Michael "High Resolution Virtual Reality." Proceedings of SIGGRAPH '92, Computer Graphics, 26(2), 1992, pp. 195-202.
Depiero et al., "3-D Computer Vision Using Structured Light: Design, Calibration and Implementation Issues," The University of Tennessee, pp. 1-46, (1996).
Dodd, G.D. et al. "Minimally invasive treatment of malignant hepatic tumors: at the threshold of a major breakthrough." Radiographies 20(1),2000, pp. 9-27.
Drascic et al., "Perceptual Issues in Augmented Reality," SPIE vol. 2653: Stereoscopic Displays and Virtual Reality Systems III, pp. 123-134 (Feb. 1996).
Dumoulin, C.L. et al., Real-Time Position Monitoring of Invasive Devices Using Magnetic Resonance, Magnetic Resonance in Medicine, vol. 29, Issue 3, Mar. 1993, pp. 411-415.

(56) References Cited

OTHER PUBLICATIONS

Fahey et al., "Meta-analysis of Pap Test Accuracy; American Journal of Epidemiology," 1995 141(7):680-689; The John Hopkins University School of Hvqiene and Public Health; USA.

Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).

Fronheiser et al., Real-Time 3D Color Doppler for Guidance of Vibrating Interventional Devices, IEEE Ultrasonics Symposium, pp. 149-152 (2004).

Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications /AugRealVis_LaparoSurg98.pdf, printed Sep. 20, 2007, 10 pages.

Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.

Fuchs, et al.: "Virtual Environments Technology To Aid Needle Biopsies of the Breast," Health Care in the Information Age, Ch. 6, pp. 60-61, Presented in San Diego, Jan. 17-20, 1996, published by IOS Press and Ohmsha Feb. 1996.

Fuhrmann A. et al., Comprehensive calibration and registration procedures for augmented reality; Proc. Eurographics Workshop on Virtual Environments 2001,219-228 (2001).

Garrett, William F. et al., "Real-Time Incremental Visualization of Dynamic Ultrasound Volumes Using Parallel BSP Trees, "Proceedings of IEEE Visualization 1996, pp. 235-240, available from www.cs.unc.edu/~andrei/pubs/1996_VIS_dualBSP_Mac.pdf, printed Sep. 20, 2007, 7 pages.

Georgakoudi et al., "Trimodal spectroscopy for the detection and characterization of cervical precancers in vivo," American Journal of Obstetrics and Gynecology; Mar. 2002; 186(3):374-382; USA.

StereoMirror Technology Webpage, http://www.planar.com/products/flatpanel_monitors/stereoscopic/(Printed Dec. 29, 2011).

Herline et al., Surface Registration for Use in Interactive, Image-Guided Liver Surgery, Computer Aided Surgery 5:11-17 (2000).

Holloway, R.; Registration Error Analysis for Augmented Reality; Presence: Teleoperators and Virtual Environments 6(4), 413-432 (1997).

Hornung et al., "Quantitative near-infrared spectroscopy of cervical dysplasia in vivo," Human Reproduction; 1999; 14(11):2908-2916; European Society of Human Reproduction and Embryology.

Howard, M.D., et al.: "An Electronic Device for Needle Placement during Sonographically Guided Percutaneous Intervention", Radiology 2001; 218:905-911.

InnerAim Brochure; 3D Visualization Software for Simpler, Safer, more Precise Aiming, Published no earlier than Apr. 1, 2010.

InVision System Brochure; A "GPS" for Real-Time 3D Needle Visualization & Guidance, Published no earlier than Mar. 1, 2008.

InVision User Manual; Professional Instructions for Use, Published no earlier than Dec. 1, 2008.

Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.

Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.

Kadi, A Majeed, et al., Design and Simulation of an Articulated Surgical Arm for Guiding Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.

Kanbara et al., "A Stereoscopic Video See-through Augmented Reality System Based on Real-time Vision-Based Registration," Nara Institute of Science and Technology, pp. 1-8 (2000).

Kato, Amami, et al., A frameless, armless navigational system for computer-assisted neurosurgery, Journal of Neurosurgery, vol. 74, No. 5, May 1991, pp. 845-849.

Keller et al., "What is it in Head Mounted Displays (MDs) that really make them all so terrible?," pp. 1-8 (1998).

Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.

Lee, et al., "Modeling Real Objects Using Video See-Through Augmented Reality," Proceedings of the Second International Symposium on Mixed Reality, ISMR 2001, pp. 19-26 (Mar. 14-15, 2001).

Lee et al., "Modeling Real Objects Using Video See-Through Augmented Reality," Presence, 11(2):144-157 (Apr. 2002).

Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.

Levy, et al., An Internet-Connected, Patient Specific, Deformable Brain Atlas Integrated into a Surgical Navigation System, Journal of Digital Imaging, vol. 10, No. 3. Suppl. 1 (August), 1997: pp. 231-237.

Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.

Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).

Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 8 pages.

Milgram et al., "Adaptation Effects in Stereo due to Online Changes in Camera Configuration," SPIE vol. 1669-13, Stereoscopic Displays and Applications III, 17 pages (1992).

Mitchell et al., "Colposcopy for the Diagnosis of Squamous Intraepithelial lesions: A metaanalysis," Obstetrics and Gynecology; Apr. 1998; 91(4):626-631.

Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.

Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.

Ohbuchi et al. "An Incremental Volume Rendering Algorithm for Interactive 3D Ultrasound Imaging", UNC-CH Computer Science Technical Report TR91-003, (1991).

Ohbuchi et al., "Incremental Volume Reconstruction and Rendering for 3D Ultrasound Imaging," Visualization in Biomedical Computing, SPIE Proceedings, pp. 312-323, (Oct. 13, 1992).

Ohbuchi, "Incremental Acquisition and Visualization of 3D Ultrasound Images," Ph.D. Dissertation, UNC-CH Computer Science Technical Report TR95-023, (1993).

PCT, International Search Report and Written Opinion, re PCT Application No. PCT/US2010/024378, dated Oct. 13, 2010.

PCT, International Search Report and Written Opinion, re PCT Application No. PCT/US2010/043760, dated Mar. 3, 2011.

PCT, The International Search Report and Written Opinion of the International Searching Authority, dated Sep. 9, 2009, for case PCT/US2009/032028.

Pogue, Brian W. et al., "Analysis of acetic acid-induced whitening of high-grade squamous intraepitheliallesions," Journal of Biomedical Optics; Oct. 2001; 6(4):397-403.

(56) References Cited

OTHER PUBLICATIONS

Ram, A.B., et al., Comparing Interpersonal Interactions with a Virtual Human to Those with a Real Human; IEEE Transactions on Visualization and Computer Graphics 13(3), 443-457 (2007).
Raz et al., Real-Time Magnetic Resonance Imaging-Guided Focal Laser Therapy in Patients with Low-Risk Prostate Cancer, European Urology 58, pp. 173-177. Mar. 12, 2010.
Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Screenshots from video produced by the University of North Carolina, produced circa 1992.
"Sony Introduces Head-Mounted Display for Endoscopic Surgery" (Jul. 23, 2013), retrieved Sep. 27, 2016, 5 pages, available at http://www.medgaget.com/2013/07/sony-introduces-head-mounted-display-for-endoscopic-surgery.html.
"Sony Introduces 'head-mount image processing unit' for endoscopic image display" (Jul. 23, 2013), retrieved Sep. 27, 2016, 14 pages, available at http://www.sony.net/SonyInfo/News/Press/201307/13-085E/index.html.
State et al., "Case Study: Observing a vol. Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.
State et al., "Interactive Volume Visualization on a Heterogeneous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.
State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking and Magnetic Tracking," ACM SIGGRAPH Computer Graphics, Proceedings of SIGGRAPH 1996, 10 pages (Aug. 1996).
State et al., "Superior Augmented Reality Registration by Integrating Landmark Tracking and Magnetic Tracking," ACM SIGGRAPH Computer Graphics, Proceedings of SIGGRAPH 1996, pp. 429-438, available from www.cs.princeton.edu/courses/archive/fall01/cs597d/papers/state96.pdf, printed Sep. 20, 20007, 10 pages.
State et al., "Technologies for Augmented Reality Systems: Realizing Ultrasound-Guided Needle Biopsies," Proc. SIGGRAPH 96 (New Orleans, LA, Aug. 4-9, 1996). In Computer Graphics Proceedings, Annual Conference Series, 1996, ACM SIGGRAPH, pp. 439-446.
State, Andrei "Exact Eye Contact with Virtual Humans." Proc. IEEE International Workshop on Human Computer Interaction 2007 (Rio de Janeiro, Brazil, Oct. 20, 2007), pp. 138-145.
State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.
Symons et al., "What are You Looking at? Acuity for Triadic Eye Gaze," J. Gen. Psychology 131(4), pp. 451-469 (2004).
Takacs et al., "The Virtual Human Interface: A Photorealistic Digital Human," IEEE Computer Graphics and Applications 23(5), pp. 38-45 (2003).
Takagi et al., "Development of a Stereo Video See-through HMD for AR Systems," IEEE, pp. 68-77 (2000).
Takayama et al., "Virtual Human with Regard to Physical Contact and Eye Contact," Entertaining Computing 2005, LNCS, vol. 3711, pp. 268-278 (2005).
Ultraguide 1000 System, Ultraguide, www.ultraguideinc.com, 1998.
Van Staveren et al., "Light Scattering in Intralipid-10% in the wavelength range of 400-1100 nm," Applied Optics; Nov. 1991; 30(31):4507-4514.
Viola et al., "Alignment by Maximization of Mutual Information," International Journal of Computer Vision, vol. 24, No. 2, pp. 137-154 (1997).
Viola, Paul A., Alignment by Maximization of Mutual Information, Ph.D. Dissertation, MIT-Artificial Intelligence Laboratory Technical Report No. 1548 (Jun. 1995), 156 pages.
Ware et al., "Dynamic Adjustment of Stereo Display Parameters," IEEE Transactions on Systems, Many and Cybernetics, 28(1):1-19 (1998).
Watson et al., "Using Texture Maps to Correct for Optical Distortion in Head-Mounted Displays," Proceedings of the Virtual Reality Annual Symposium '95, IEEE, pp. 1-7 (1995).
Welch, Hybrid Self-Tracker: An Inertial/Optical Hybrid Three-Dimensional Tracking System, University of North Carolina Chapel Hill Department of Computer Science, TR 95-048 (1995).
Yinghui et al., Real-Time Deformation Using Modal Analysis on Graphics Hardware, GRAPHITE 2006, Kuala Lumpur, Malaysia, Nov. 29-Dec. 2, 2006.
Zitnick et al., "Multi-Base Stereo Using Surface Extraction," Visual Interface Inc., (Nov. 24, 1996).
"AIM 3D Needle Placement Software from InnerOptic", Medgadget, Sep. 21, 2012.
AIM Section 5: 510k Summary, submitted by InnerOptic Technology, Inc., in 5 pages, submission date May 17, 2012.
"InnerOptic's AIM System Receives DA 510(K) Clearance", InnerOptic Technology, Inc., Sep. 18, 2012.
Lindeman, A Low-Cost, Low-latency Approach to Dynamic Immersion in Occlusive Head-Mounted Displays, University of Canterbury, WPI,—Poster from IEEE VR 2016, Mar. 19-23, 2016.
Ohnesorge, Lauren K., "InnerOptic technology wins FDA approval", Triangle Business Journal, Sep. 19, 2012.
Press Release: Pathfinder and InnerOptic Announce Technology Integration to Enhance Visualization and Outcomes in Liver Surgery, Published Mar. 6, 2013.
Edwards et al., Video See-Through Design for Merging of Real and Virtual Environments, VRAIS '93, pp. 1-11 (1993).
Lipton, "Foundations of the Steroscopic Cinema A Study in Depth," Van Nostrad Reinhold Company, pp. 1-319 (1982).
FUHRMANN al, Comprehensive calibration and registration procedures for augmented reality; Proc. Eurographics Workshop on Virtual Environments 2001, 219-228 (2001).

* cited by examiner

SYSTEMS, METHODS, APPARATUSES, AND COMPUTER-READABLE MEDIA FOR IMAGE GUIDED SURGERY

CROSS-REFERENCE TO RELATED APPLICATIONS

This application is a continuation of U.S. application Ser. No. 15/182,346, filed on Jun. 14, 2016, which is a continuation of U.S. application Ser. No. 14/166,173, filed on Jan. 28, 2014, now U.S. Pat. No. 9,398,936, issued on Jul. 26, 2016, which is a continuation of U.S. application Ser. No. 12/703,118, filed on Feb. 9, 2010, now U.S. Pat. No. 8,690,776, issued on Apr. 8, 2014, which claims the benefit of U.S. Provisional Application No. 61/207,593, filed Feb. 17, 2009, U.S. Provisional Application No. 61/207,589, filed Feb. 17, 2009, and U.S. Provisional Application No. 61/207,592, filed Feb. 17, 2009, each of which is incorporated by reference herein in its entirety for all purposes.

FIELD

The embodiments disclosed relate to computer-assisted surgery and more specifically related to systems, methods, apparatuses, and computer-readable media for image-guided surgery.

BACKGROUND

The past few decades have seen incredible development of technology and systems for computer assisted, image based, or image guided surgery. The advances in image guided surgery are tied in part to technological and scientific improvements in imaging and 3D computer graphics. For example, the early work of Mark Levoy, Turner Whitted, Richard Holloway, and Stephen Pizer in the late 1980s provided new 3D computer graphics rendering techniques, medical image shape detection, and head-mounted displays. These are some of the building blocks of later image-guided surgery systems built at the University of North Carolina in the mid 1990s and after.

Image guided surgery makes use of imaging to aid the surgeon to perform more effective or more accurate surgery. As merely one example of such image guided surgery, the use of ultrasound to guide needles being inserted into the liver for ablation are used by the surgeon to help guide the needle.

Current systems, however, have inadequate visualizations of image guidance data. This inadequate data may include the lack of useful information regarding an ablation needle and its potential effect on the procedure. Also, the equipment used for image guided surgery is typically difficult to calibrate. For example, each time a practitioner uses a new surgical instrument that must be optically tracked by an image guidance system, she must perform the following two steps. First, she must rigidly affix the tracking fiducials to the needle. This may involve tightening screws, or to threading a needle through a hole or tube. Second, she must measure the position of the tip of the needle, relative to the fiducials. This may involve manually measuring the surgical instrument length with a ruler, and then entering this information into a workstation; or using a dedicated calibration rig, and perform a lengthy (e.g., several minute) calibration process.

These problems and others are addressed by the systems, methods, devices and computer-readable media described herein.

SUMMARY

Presented herein are methods, systems, devices, and computer-readable media for image guided surgery. In some embodiments, a system may determine device type information for a first medical device; real-time emplacement information for the first medical device; and real-time emplacement information for a second medical device. The system may also determine the real-time relative emplacements of the first and second medical devices with the computer system and real-time prediction information for the first medical device. The image guidance system may then generate image guidance information based on the real-time relative emplacements of the first and second medical devices, the real-time prediction information for the first medical device, and data related to the second medical device. A graphical rendering of the image guidance information may be displayed on one or more displays.

Numerous other embodiments are described throughout herein. Although various embodiments are described herein, it is to be understood that not necessarily all objects, advantages, features or concepts need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

DETAILED DESCRIPTION OF SPECIFIC EMBODIMENTS

Overview

Figure 3A:
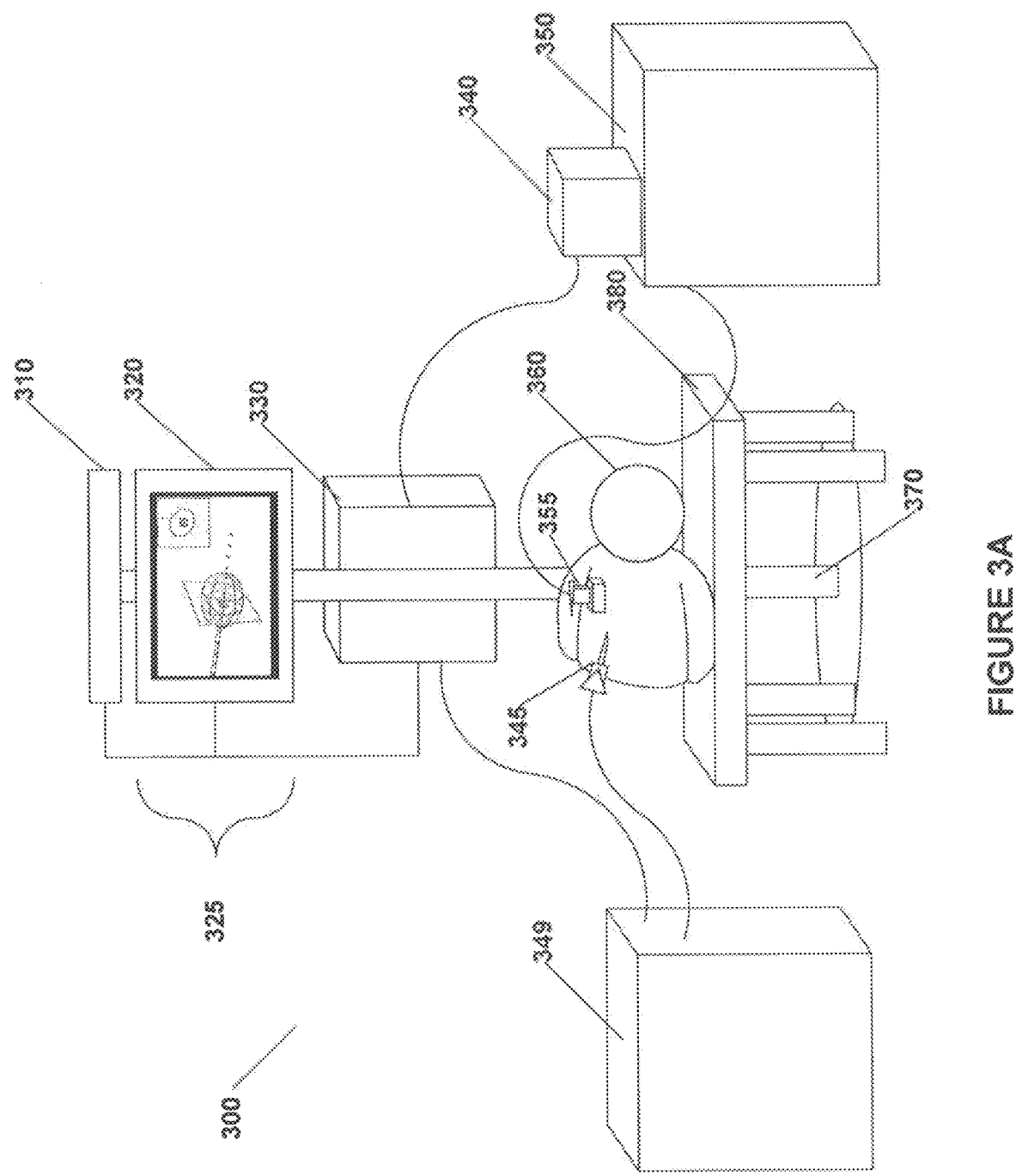
FIG. 3A illustrates a first exemplary system for image guided surgery.
Figure 3B:
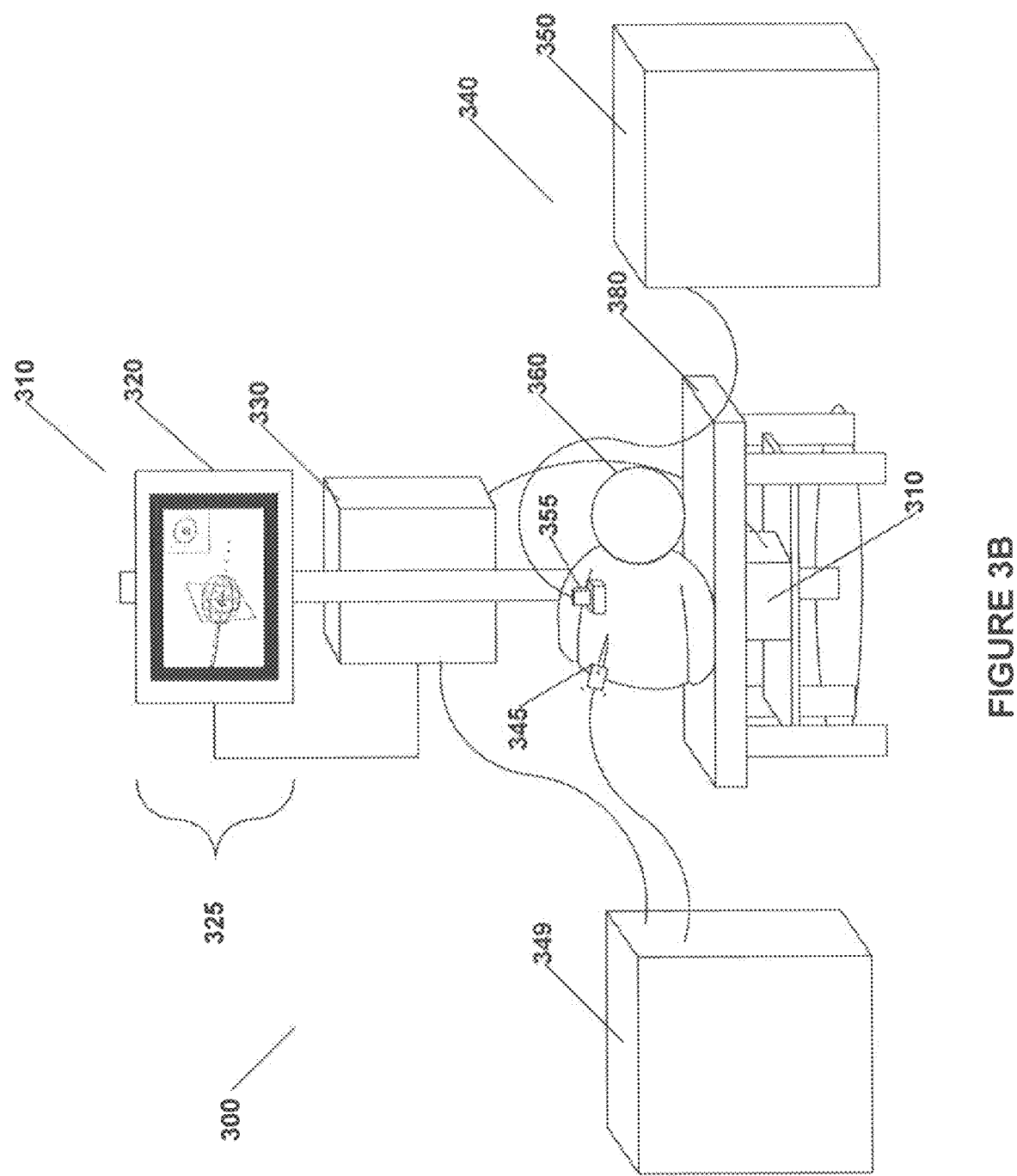
FIG. 3B illustrates a second exemplary system for image guided surgery.

In some embodiments, a system, such as depicted in FIGS. 3A and 3B, may track a surgical instrument, such as an ablation needle, and an imaging device, such as an ultrasound wand. In other embodiments, numerous other medical or surgical devices may be tracked, and the system may track three, four, or more of medical or surgical devices or medical devices. A "medical device" is a term that may include surgical devices and non surgical devices and all of those terms are broad terms and are intended to encompass their plain and ordinary meaning, including without limitation, ablation needles, scalpels, endoscopes, ultrasound wands, etc. Information about the surgical or medical devices may be predicted or determined and displayed by the system in 2D or 3D on a display visible to physician using the system. "Prediction information" is a broad term and is intended to encompass its plain and ordinary meaning, including without limitation, image guidance data, mathematical data, mathematical or 3D models related to a procedure, etc.

As an example embodiment, the system may determine or predict the intersection point of an ultrasound slice and the projection of an ablation needle. The system may also compute and display relative orientation information, and, in the case of collected 3D data, such as 3D ultrasound data, the system may segment and display the data in different manners, such as in 2D slices, 3D volumes, etc. This "extra" data displayed to the physician may be useful as it provides the physician with more information about the operation, the instruments, and/or data from the instruments.

Embodiments herein may be used for many kinds of needle-based medical procedures, including, but not limited to, radiofrequency-, cryo-, microwave-, laser-ablation of tumors, fibroids, lesions, etc, as well as biopsies, injections, central line placements, cyst aspirations, fluid drainings, lumpectomies, and guidance of wires and stents through blood vessels and ducts. Herein, the term needle to refer to any rigid needle-like object, such as an ablation antenna or probe, cannula, catheter, electro-cautery device, Bovie, laser waveguide, stent application device, etc. Needle may also refer to a non-rigid or nearly rigid version of the above. The system may also be used with non-needle devices such as scalpels, forceps, cutting loops on hysteroscopes, harmonic sheers, lasers (including $CO_2$ lasers), etc.

Some embodiments include tracking fixtures that may mount to surgical or medical devices, such as ablation needles, ultrasound wands, ultrasound probes, scalpels, etc. that allow for quicker attachment and easier tracking calibration for the devices. These embodiments may allow a physician to more quickly and easily start using the system.

Exemplary Systems

FIG. 3A illustrates a first exemplary system for image guided surgery. FIG. 3B illustrates a second exemplary system for image guided surgery. In many respects the embodiments illustrated by FIGS. 3A and 3B are similar and use similar numbering. Where the two are different, those differences are noted. The differences between the two figures may include that, in FIG. 3A, two position sensing units 310 and 340 are shown, whereas in FIG. 3B, only a single position sensing unit 310 is shown.

In some embodiments, position sensing units 310 and 340 may be tracking systems 310 and 340 and may track surgical instruments 345 and 355 and provide data to the image guidance unit 330. The image guidance unit 330 may process or combine the data and show image guidance data on display 320. This image guidance data may be used by a physician to guide a procedure and improve care. There are numerous other possible embodiments of system 300. For example, numerous of the depicted modules may be joined together to form a single module and may even be implemented in a single computer or machine. Further, position sensing units 310 and 340 may be combined and track all relevant surgical instruments 345 and 355, as discussed in more detail below and exemplified in FIG. 3B. Additional imaging units 350 may be included and combined imaging data from the multiple imaging units 350 may be processed by image guidance unit 330 and shown on display unit 320. Additionally, surgical systems 349 may also be included. Information about and from multiple surgical systems 349 and attached surgical instruments 345 may be processed by image guidance unit 330 and shown on display 320. These and other possible embodiments are discussed in more detail below.

In some embodiments, system 300 comprises a first position sensing unit 310, a display unit 320, and second position sensing unit 340 (if it is included) all coupled to image guidance unit 330. In some embodiments, first position sensing unit 310, display unit 320, and image guidance unit 330 are all physically connected to stand 370. Image guidance unit 330 may be used to produce images 325 that are displayed on display unit 320. The images 325 produced on display unit 320 by the image guidance unit 330 may be determined based on ultrasound or other visual images from first surgical instrument 345 and second surgical instrument 355. For example, if first surgical instrument 345 is an ablation needle 345 and second surgical instrument 355 is an ultrasound wand 355, then images 325 produced on display 320 may include the video from the ultrasound wand 355 combined with graphics, such as projected needle drive or projected ablation volume, determined based on the emplacement of ablation needle 345. If first surgical instrument 345 is an ultrasound wand 345 and second surgical instrument 355 is a laparoscopic camera 355, then images 325 produced on display 320 may include the video from the laparoscopic camera 355 combined with ultrasound data superimposed on the laparoscopic image. More surgical instrument may be added to the system. For example, the system may include an ultrasound wand, ablation needle, laparoscopic camera, cauterizer, scalpel and/or any other surgical instrument. The system may also include in the processing previously collected data, such as preoperative CT scans, X-Rays, MRIs, etc.

Emplacement as used herein may refer to pose, position, orientation, the combination or position and orientation, or any other appropriate location information. In some embodiments, the imaging data obtained from one or both of surgical instruments 345 and 355 may include other modalities such as a CT scan, MRI, open-magnet MRI, optical coherence tomography, positron emission tomography ("PET") scans, fluoroscopy, ultrasound, or other preoperative or intraoperative 2D or 3D anatomical imaging data. In some embodiments, surgical instruments 345 and 355 may also be scalpels, implantable hardware, or any other device used in surgery. Any appropriate surgical system 349 or imaging unit 350 may be attached to the corresponding medical instruments 345 and 355.

As noted above, images 325 produced may also be based on live, intraoperative, or real-time data obtained using second surgical instrument 355, which is coupled to second imaging unit 350. As used herein, real-time data may be that data that is obtained at a frequency that would allow a surgeon to meaningfully interact with the data during surgery. For example, in some embodiments, real-time data may be a medical image of a patient that is updated one time per second. In some embodiments, real-time data may be ultrasound data that is updated multiple times per second. Second surgical instrument 355 may be coupled to second position sensing unit 340. Second position sensing unit 340 may be part of imaging unit 350 or it may be separate. Second position sensing unit 340 may be used to determine the emplacement of second surgical instrument 355. In some embodiments, first and/or second position sensing units 310 and/or 340 may be magnetic trackers and magnetic may be coils coupled to surgical instruments 345 and/or 355. In some embodiments, first and/or second position sensing units 310 and/or 340 may be optical trackers and visually-detectable fiducials may be coupled to surgical instruments 345 and/or 355.

Images 325 may be produced based on intraoperative or real-time data obtained using first surgical instrument 345, which is coupled to first surgical system 349. In FIGS. 3A and 3B, first surgical system 349 is shown as coupled to image guidance unit 330. The coupling between the first surgical system 349 and image guidance unit 330 may not be present in all embodiments. In some embodiments, the coupling between first surgical system 349 and image guidance unit 330 may be included where information about first surgical instrument 345 available to first surgical system 349 is useful for the processing performed by image guidance unit 330. For example, in some embodiments, first surgical instrument 345 is an ablation needle 345 and first surgical system 349 is an ablation system 349. In some embodiments, it may be useful to send a signal about the relative strength of planned ablation from ablation system 349 to image guidance unit 330 in order that image guidance unit 330 can show a predicted ablation volume. In other embodiments, first surgical system 349 may not be coupled to image guidance unit 330. Example embodiments including images and graphics that may be displayed are included below.

In some embodiments, first position sensing unit 310 tracks the emplacement of first surgical device 345. First position sensing unit 310 may be an optical tracker 310 and first surgical device 345 may have optical fiducials attached thereto. The emplacement of optical fiducials may be detected by first position sensing unit 310, and, therefrom, the emplacement of first surgical device 345 may be determined.

In various embodiments, as depicted in FIG. 3B, a single position sensing unit 310 may track both first medical device 345 and second medical device 355. In FIG. 3B, in some embodiments, position sensing unit 310 is a magnetic tracker and is mounted below a surgical table 380. Such an arrangement may be useful when the tracking volume of the position sensing unit 310 is dependent on the location of the position sensing unit, as with many magnetic trackers. Magnetic tracking coils may be mounted in or on the medical devices 345 and 355.

In some embodiments, either or both of the first position sensing unit 310 and the second position sensing unit 340 may be an Ascension Flock of Birds, Nest of Birds, drive-BAY, medSAFE, trakSTAR, miniBIRD, MotionSTAR, pci-BIRD, or Calypso 4D Localization System and tracking units attached to the first and/or second surgical or medical devices 345 and 355 may be magnetic tracking coils. In some embodiments, either or both of the first position sensing unit 310 and the second position sensing unit 340 may be an Aurora® Electromagnetic Measurement System using sensor coils for tracking units attached to the first and/or second surgical devices 345 and 355. In some embodiments, either or both of the first position sensing unit 310 and the second position sensing unit 340 may also be an optical 3D tracking system using fiducials. Such optical 3D tracking systems may include the NDI Polaris Spectra, Vicra, Certus, PhaseSpace IMPULSE, Vicon MX, InterSense IS-900, NaturalPoint OptiTrack, Polhemus Fast-Trak, IsoTrak, or Claron MicronTracker2. In some embodiments, either or both of position sensing units 310 and 340 may be attached to or affixed on the corresponding surgical device 345 and 355. In some embodiments, the position sensing units, 310 and 340, may include sensing devices such as the HiBall tracking system, a GPS device or signal emitting device that would allow for tracking of the position and, optionally, orientation of the tracking unit. In some embodiments, a position sensing unit 310 or 340 may be affixed to either or both of the surgical devices 345 and 355. The surgical devices 345 or 355 may be tracked by the position sensing units 310 or 340. A world reference, such as the display 320 may also be tracked by the position sensing unit 310 or 340 in order to determine the emplacements of the surgical devices 345 and 355 with respect to the world. Devices 345 and 355 may also include or have coupled thereto one or more accelerometers, which may be used to estimate movement, position, and location of the devices.

In some embodiments, the display unit 320 displays 3D images to a physician. Stereoscopic 3D displays separate the imagery shown to each of the user's eyes. This can be accomplished by a stereoscopic display, a lenticular auto-stereoscopic display, or any other appropriate type of display. The display 320 may be an alternating row or alternating column display. Example alternating row displays include the Miracube G240S, as well as Zalman Trimon Monitors. Alternating column displays include devices manufactured by Sharp, as well as many "auto-stereoscopic" displays (e.g., Philips). Display 320 may also be a cathode ray tube. Cathode Ray Tube (CRT) based devices, may use temporal sequencing, showing imagery for the left and right eye in temporal sequential alternation; this method may also be used by newer, projection-based devices, as well as by 120-Hz-switchable liquid crystal display (LCD) devices.

In some embodiments, a user may wear a head mounted display in order to receive 3D images from the image guidance unit 330. In such embodiments, a separate display, such as the pictured display unit 320, may be omitted. The 3D graphics may be produced using underlying data models, stored in the image guidance unit 330 and projected onto one or more 2D planes in order to create left and right eye images for a head mount, lenticular or other 3D display. The underlying 3D model may be updated based on the relative emplacements of the various devices 345 and 355, as determined by the position sensing unit(s), and/or based on new data associated with the devices 345 and 355. For example, if the second device is an ultrasound wand 355, then the underlying data model may be updated to reflect the most recent ultrasound image. If the first device 345 is an ablation needle, then the underlying model may be updated to reflect any changes related to the needle, such as power or duration information. Any appropriate 3D graphics processing may be used for rendering including processing based on OpenGL, Direct3D, Java 3D, etc. Whole, partial, or modified 3D graphics packages may also be used, such packages including 3DS Max, SolidWorks, Maya, Form Z, Cybermotion 3D, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

There are numerous other examples of image guidance systems which may use, incorporate, support, or provide for the techniques, methods, processes, and systems described herein, such as the 3D computer-graphics-based assigned to InnerOptic Technologies, Inc. that provides for displaying guidance data from multiple sources, U.S. application Ser. No. 11/833,134, filed Aug. 2, 2007, the contents of which are incorporated herein in their entirety for all purposes.

Image Guidance Processes and Data

Depicting Surgical Instruments

Figure 4:
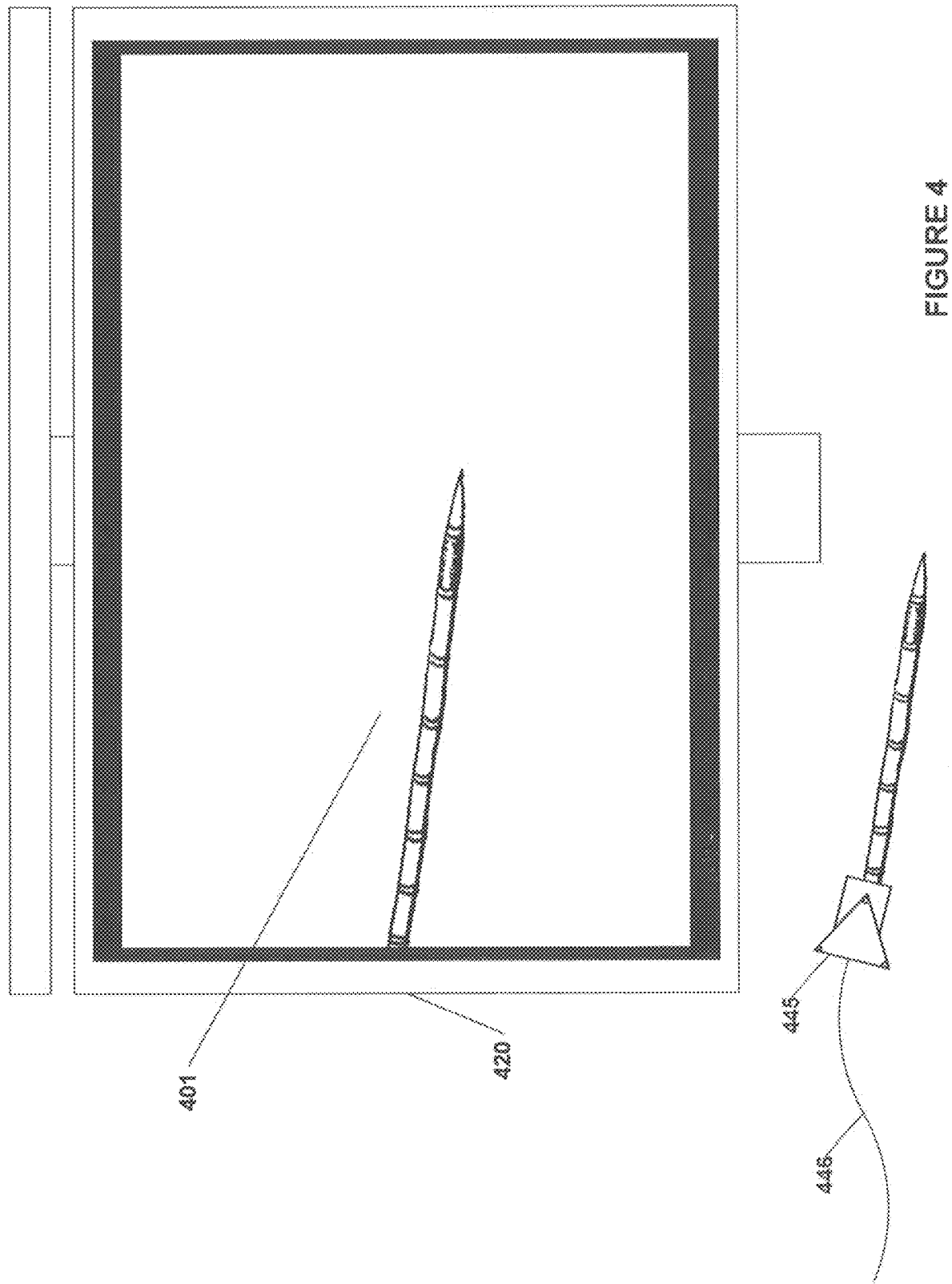
FIG. 4 illustrates a first example of displaying image guidance data.

Previous systems do not provide satisfactory image guidance data. It can often be difficult to discern the content of a 3D scene from a 2D depiction of it, or even from a 3D depiction of it. Therefore, various embodiments herein provide image guidance that can help the doctor better understand the scene, relative emplacements or poses of object in the scene and thereby provide improved image guidance. FIG. 4 illustrates an image 401 of an exemplary surgical instrument 445 being displayed on a screen 420. In this case, the surgical instrument displayed is an ablation needle 445. Also depicted is the wire 446 connecting the ablation needle to an ablation system. Some models of needles have markings such as bands around the shaft (to indicate distance along the shaft), and a colored region near the tip to indicate where the radio frequency or microwave energy is emitted from in the case of an ablation probe. Physicians performing needle procedures are often familiar with these markings and may use them to help understand the spatial relationship between the needle and anatomy. In some embodiments, the make and model of the needle 445 is known to the image guidance system and the needle displayed (401) in display 420 may resemble needle 445. The features of needles that may be rendered in the scene include the overall shape (diameter, cross sectional shape, curvature, etc.), color, distance markers, visuals or echogenic fiduciary markers, the state of deployable elements such as tines, paddles, anchors, resection loops, stiffening or steerable sleeves, temperature, radiation, light or magnetic field sensors, lens, waveguides, fluid transfer channels, and the like.

The type of needle being used may be input into the image guidance system, may be a system default, may be detected by a camera or other device, may be received as data from an attached medical device, such as surgical system 349 in FIGS. 3A and 3B, or the information may be received in any other appropriate manner. Making the surgical instrument displayed on display 420 resemble the surgical instrument 445 may help physicians associate the image guidance data with the real world and may provide more familiar guidance information to a physician, thereby further aiding the physician in the guidance task. For example, the surgeon may see the familiar markings on the needle being displayed on the display 420 and therefore be familiar with the distance and relative placement of the displayed needle with respect to other data, such as a tumor seen in an ultrasound (not depicted in FIG. 4). This knowledge of relative placement of items being displayed may help the surgeon get the needle into place.

Consider an embodiment in which the image in the display 420 has a needle depicting the portion of the needle that will perform the ablation, for example, the portion that emits the radio or microwave energy. If the display 420 also includes ultrasound data, then the doctor may be able to find the tumor she wishes to ablate by moving the ultrasound wand around until she spots the tumor. In various embodiments, she will be able to see the displayed ultrasound data and its location relative to the displayed needle with the markings. She can then drive the needle until she sees, on display 420, that the emitter-portion of the needle encompasses the tumor in the ultrasound, also seen on display 420. When she activates the ablation, she can then be much more certain that she has ablated the correct portion of the tissue. Various embodiments of this are discussed more below.

As another example, consider the physical markings that may be on the instruments themselves. These markings can help orient a physician during use of the instrument. In some embodiments, the image guidance unit may represent these markings in the images displayed in the display. For example, certain ultrasound transducers are built with an orientation mark (e.g., a small bump) on one side of the transducing array. That mark may also be shown in the ultrasound image on the scanner's display, to help the physician understand where the scanned anatomical structures shown on screen are located under the transducer, inside the patient. In some embodiments, the image guidance system may display a symbolic 3D representation of the orientation mark both next to the motion-tracked ultrasound slice (e.g., moving with the displayed ultrasound slice) and next to the 2D ultrasound slice also displayed by the IVS. An example of this is displayed in FIG. 7, where a small rectilinear volume corresponding to a feature on an ultrasound wand is shown both in proximity to the ultrasound slice displayed in 3D and the ultrasound slice displayed as a 2D image.

Other embodiments will track and display other types of instruments and their features. For example, a surgeon may want to track one or more of a scalpel, a cauterizer (including an electrocauterizer and Bovies), forceps, cutting loops on hysteroscopes, harmonic sheers, lasers (including $CO_2$ lasers), etc. For example, in various embodiments, the following devices may be tracked and various aspects of their design displayed on display 420:

Olympus™ OES Pro Hystero-Resectoscope, SonoSurg Ultrasonic Surgical System

Olympus™ GF-UC 160 Endoscope

Wallus™ Embryo Transfer Catheter

AngioDynamics® NanoKnife™, VenaCure™ laser, StarBurst, Uniblade, Habib® Resector Bovie® Electrodes Covidien Evident™, Cool-tip™ Ablation Antennas, Opti4™ Electrodes Microsulis MEA (microwave endometrial ablation), Acculis Halt™ Medical System Optimed BigLumen Aspiration Catheter Optimed Optipure S tent Central venous catheterization introducer needle (such as those made by Bard and Arrow)

Once tracked, a physician may be able to see image guidance data on display 420 that will allow her to know the relative pose, location, or emplacement of the tracked instrument(s) with respect to one another or with respect to imaging data and will be able to see, on display 420, the features of the instrument rendered in the scene.

Depicting Ablation Volume and Other Instrument Information

Figure 5:
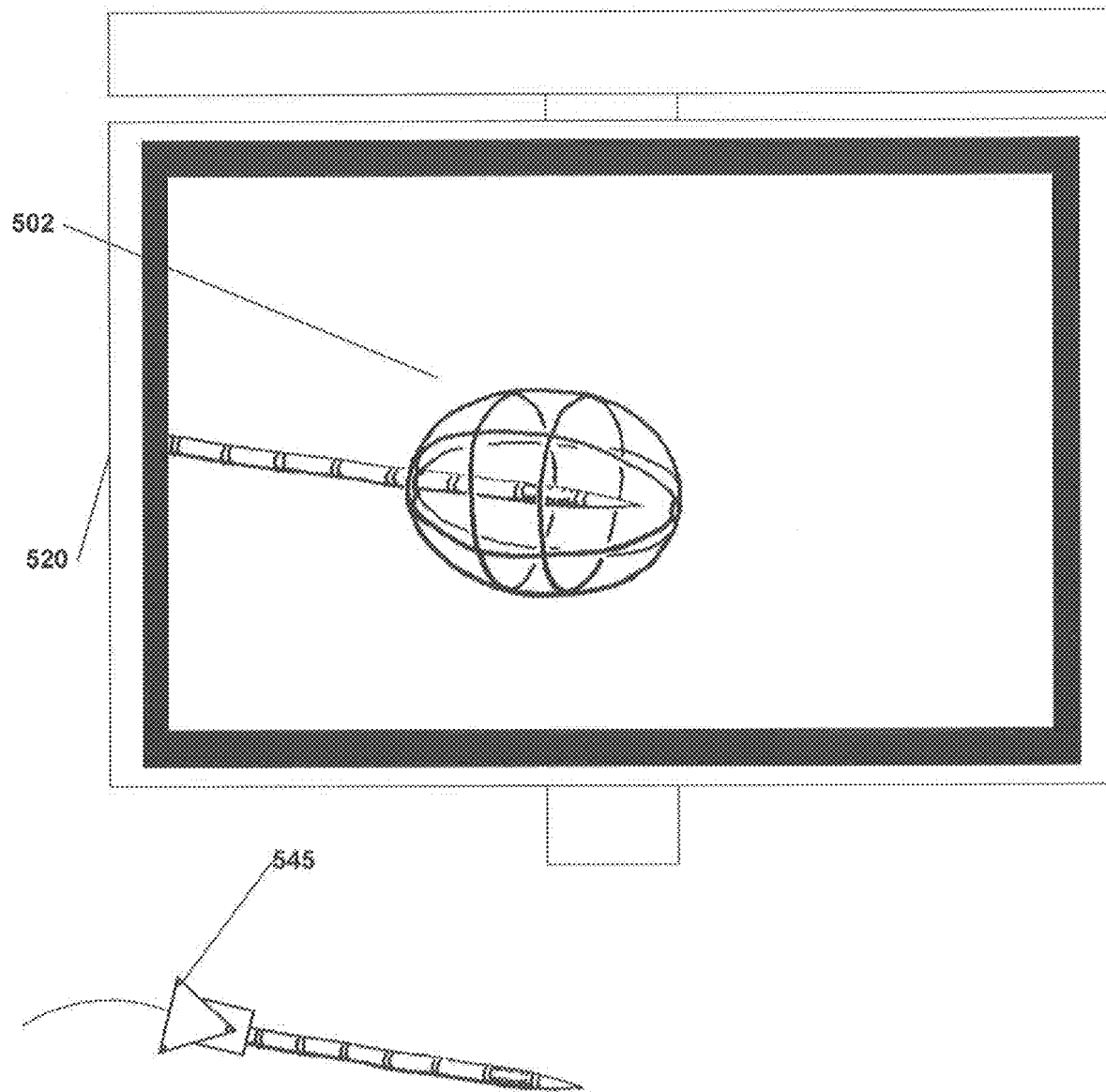
FIG. 5 illustrates a second example of displaying image guidance data.

Various embodiments of the systems herein will depict as part of the image guidance data information related to the surgical instruments. For example, in some embodiments, an image guidance system such as the systems of FIG. 3A or 3B may illustrate an expected spherical ablation volume. For example, FIG. 5 shows an ablation needle 545 which has a darkened portion that indicates where the radio frequency or microwave energy for ablation will be emitted. In some embodiments, an image guidance system may display on display 520 the expected ablation volume 502. The ablation volume 502 may be shown as a transparent volume, a wireframe volume (depicted in FIG. 5), as a point cloud of various densities, as an outline, as a volume, or in any other appropriate manner.

For some ablation needles, the expected volume of ablated tissue is neither spherical nor centered at the tip of the needle. For example: a Covidien surgical microwave needle has an ellipsoidal ablation volume; a Covidien Evident transcutaneous microwave needle has a teardrop-like ablation volume; RFA Medical's bipolar ablation system uses two needles simultaneously, where each needle has paddles that deploy after the needle is inserted inside the tissue (which one may equate to a canoe's oar). In some embodiments, the ablation volume for such a needle is, to a first approximation, a volume that lies directly between the paddles of the two needles.

The position and orientation of the volume may be specified by the placement of a tracked needle, such as needle 545 in FIG. 5. In some embodiments, with single needle ablation systems, the volume's approximate size (e.g., girth and length, if ellipsoidal) may be either specified by the physician, or automatically computed by the guidance system. The ablation volume may be based on numerous parameters such the needle make and model, power and duration settings of the microwave or radio frequency generator, measured or estimated temperature and impedance of the target tissue or other tissue information, a formula, a look-up-table, fixed or default values, or based on any other appropriate available information.

Other instrument information may also be depicted. For example, if a cauterizer is tracked as part of an image guidance system, then the cauterization volume may be determined or estimated and that volume may be displayed. If a laser is tracked as part of the image guidance system, then the projected laser path may be determined or estimated and displayed.

Depicting Needle Drive Projection and Other Prediction Information

Figure 6:
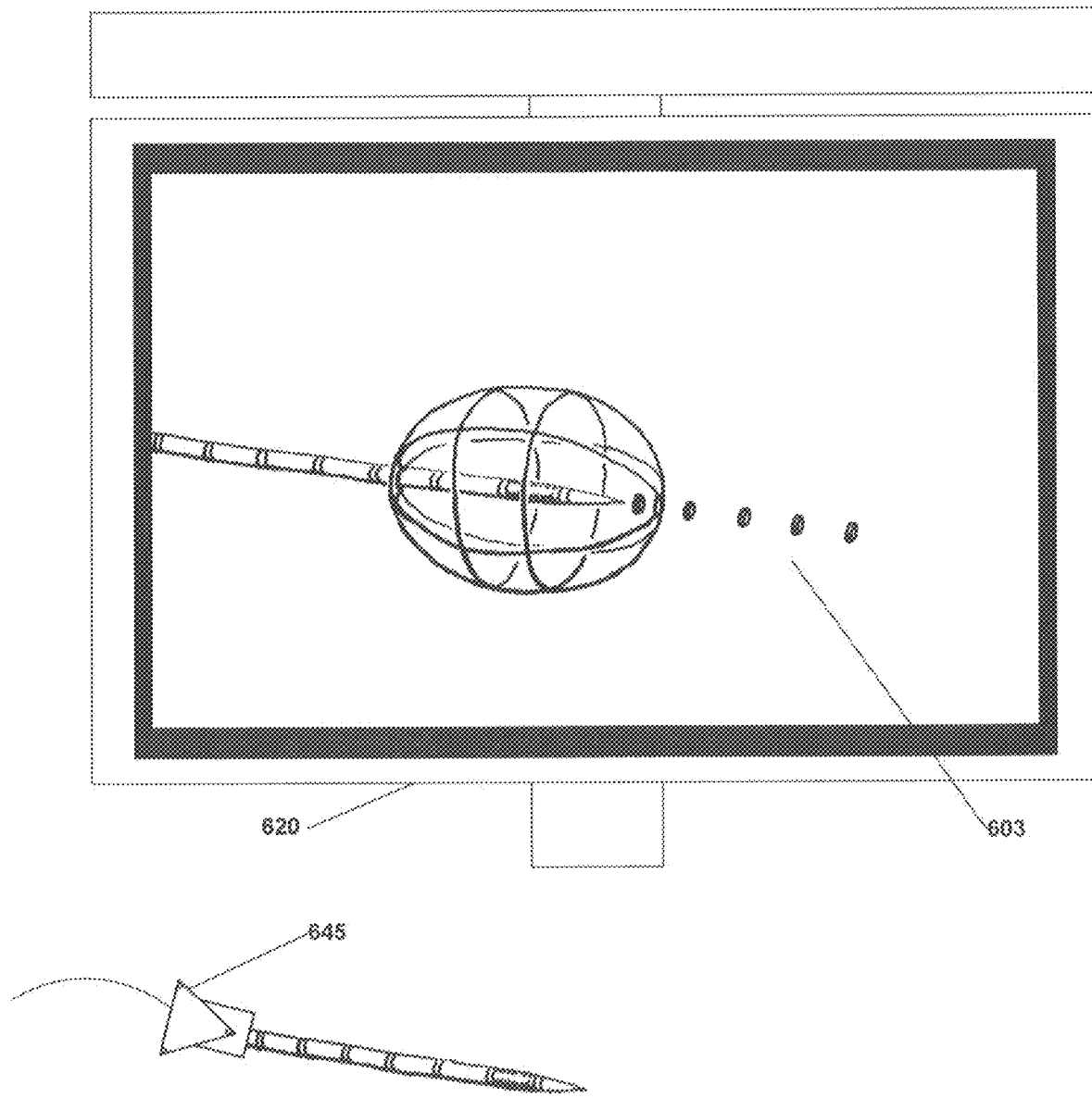
FIG. 6 illustrates a third example of displaying image guidance data.

In certain procedures, there may be prediction information related to the surgical instruments. In the context of scalpel movement, this may be the location that the scalpel will hit if a physician continues to move the scalpel in a particular direction. In the context of ablation, this may be the projected needle placement if it is driven along its central axis. FIG. 6 illustrates both an ablation volume for an ablation needle and a projected needle drive 603. If a physician is driving an ablation needle 645 into tissue (not pictured), then she may want to know where the needle will be driven. In some embodiments, the projected drive of a needle 645 may be depicted on the display 620 and may show the physician the projected path 603 that the needle will take if it is driven along its central axis.

In some embodiments, in order to aid the physician in placing or orienting a needle 645, an image guidance system, such as that depicted in FIG. 3A or FIG. 3B, may draw a number of rings about the axis of the needle shaft, extrapolated beyond its tip, as depicted in FIG. 6. A physician may view and manipulate the position and orientation of the needle 645 and its expected drive projection (via its displayed projected trajectory) before it enters the patient's tissue. In some embodiments, this is accomplished by the doctor positioning the virtual rings in the drive projection such that they are co-incident (or pass through) the ultrasound representation of a target, such as a tumor that the doctor has spotted in the ultrasound. This may allow the physician to verify that the needle 645 is properly aimed at the target and can drive the needle 645 forward into the tissue such that it reaches its desired target or destination. For example, if the doctor spotted a tumor in the ultrasound image (not pictured in FIG. 6), she may be able to align the ablation needle 645 such that the drive projection rings on display 620 intersected or otherwise indicated that the needle, if driven straight, will reach the tumor.

The rings may be spaced at regular (e.g., 0.5, 1, or 2 cm) intervals to provide the physician with visual cues regarding the distance from the needle tip to the targeted anatomy. In some embodiments, the spacing of the rings may indicate other aspects of the data, such as the drive speed of the needle, the density of the tissue, the distance to a landmark, such as the ultrasound data, or any other appropriate guidance data or property. In some embodiments, the rings or other trajectory indicator may extend beyond the needle tip, by a distance equal to the length of the needle-shaft. This way, the user knows if the needle is long enough to reach the target—even before the tip enters the patient. That is, in some embodiments, if the rings do not reach the target with the tip still outside the body, then the tip won't reach the target even when the entire length shaft is inserted into the body.

Other display markers may be used to show trajectory, such as a dashed, dotted, or solid line, transparent needle shaft, point cloud, wire frame, etc. In some embodiments, three-dimensional rings may be used and provide depth cues and obscure little of the ultrasound image. Virtual rings or other virtual markers may be displayed semi-transparently, so that they obscure less of the ultrasound image than an opaque marker would.

Other prediction information may also be displayed. For example, if a scalpel is being tracked by the image guidance system, then a cutting plane corresponding to the scalpel may be displayed (not pictured). Such a cutting plan may be coplanar with the blade of the scalpel and may project from the blade of the scalpel. For example, the projected cutting plane may show where the scalpel would cut if it were the doctor were to advance the scalpel. Similar prediction information may be estimable or determinable for cauterizers, lasers, and numerous other surgical instruments.

Depicting Combinations of Graphics

Figure 7:
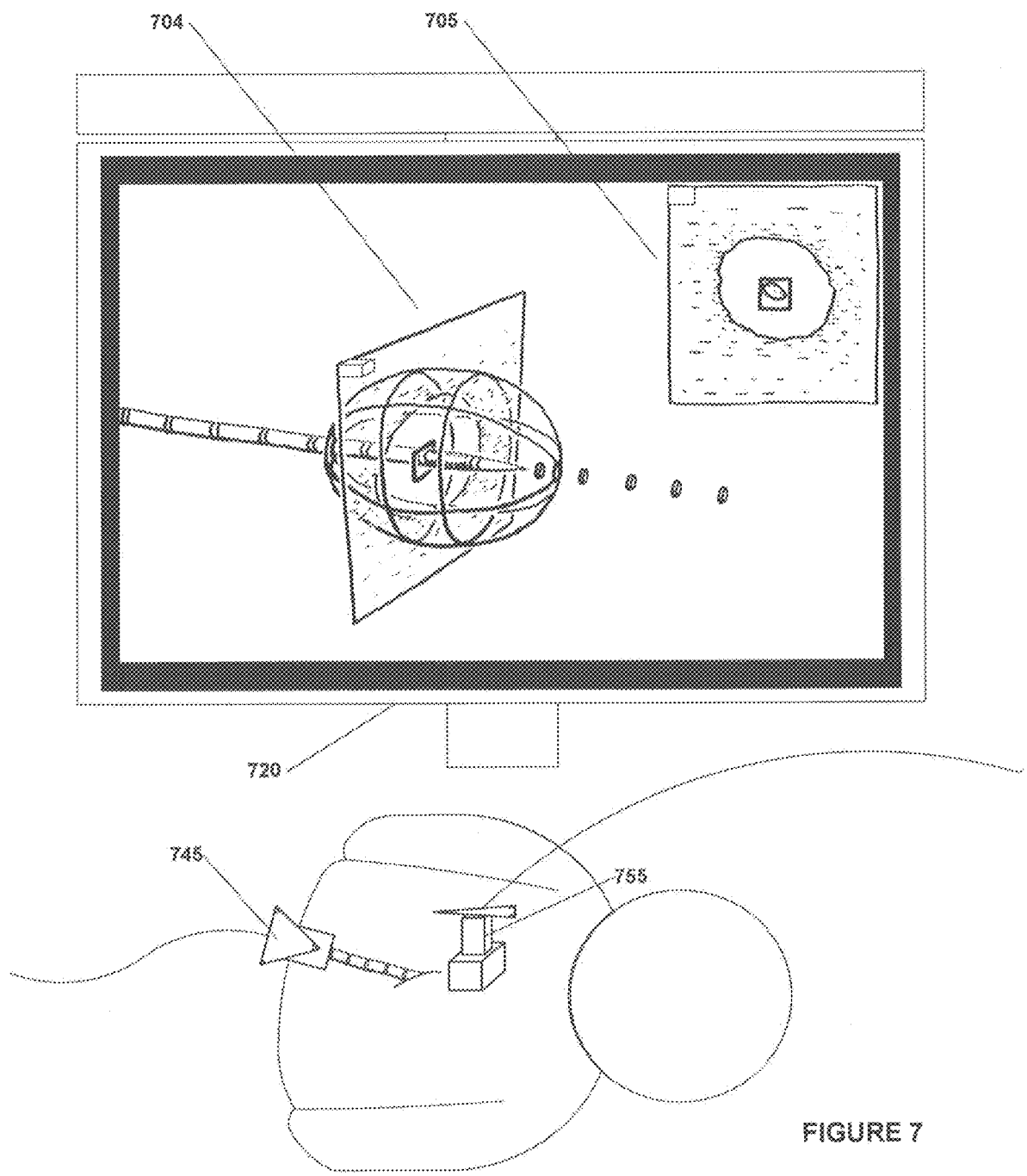
FIG. 7 illustrates a fourth example of displaying image guidance data.

As discussed herein, when there are multiple instruments or devices being used in a procedure, images, graphics, and data associated with the multiple instruments may be displayed to the physician. In some embodiments, as depicted in FIG. 7, when there are two devices 745 and 755 being used and tracked in a procedure, data, images, and graphics associated with those two images may be combinable and may be displayed on the same display. FIG. 7 depicts an ablation needle 745 and an ultrasound wand 755 being used during a procedure. Data associated with each of the devices 745 and 755 are displayed on the display 720.

The data from two or more devices may be combined and displayed based on their relative emplacements or poses. For example, an ultrasound image 704 may be displayed with respect to an ablation needle on a display 720 in a manner that estimates the relative emplacements or poses of an ultrasound wand 755 and ablation needle 745. This is depicted in FIG. 7. In FIG. 7, the graphics associated with the ablation needle 745, including the ablation volume and projected drive location are shown spatially located with the oriented planar ultrasound image on display 720. In this image 704, a tumor appears in the ultrasound image and the ablation needle is shown driven through the tumor. The ablation volume estimates where ablation would occur if it tissue were ablated at that time. The physician can see that the ablation volume appears to cover the tumor displayed in the ultrasound image.

Various embodiments include other combinations of graphics. For example, in some embodiments, data related to a single surgical instrument (such as an ablation needle, ultrasound wand, etc.) may be presented in more than one manner on a single display. Consider an embodiment in which device 745 is an ablation needle and device 755 is an ultrasound transducer. If a physician orients ultrasound transducer 755 such that it is perpendicular to the monitor, the 3D view of the ultrasound image would show only the edge and the ultrasound image would not be visible. In some embodiments, the image guidance system could track the physician's head using a position sensor, such as first and/or second position sensing units 310 and/or 340 of FIG. 3A or FIG. 3B. The physician then may be able to move her head to the side, so that she sees the ultrasound image from a different perspective.

In some embodiments, the image guidance system can constantly display an additional 2D view of the ultrasound image 705 (in screen space), simultaneous to the 3D depiction of the procedure, so that the ultrasound image is always visible, regardless of the orientation in which the physician holds the transducer. This is illustrated in FIG. 7. This display of the ultrasound data may be similar to what a physician is accustomed to seeing with traditional ultrasound displays. This may be useful to provide the physician with imaging to which she is accustomed and allows a physician to see the ultrasound data regardless of the then-current orientation of the ultrasound wand with respect to the user.

In some embodiments, the 2D view 705 of an ultrasound image is depicted in the upper right corner of the monitor (though it can be placed in any corner). The guidance system can automatically (and continually) choose a corner in which to render the 2D view of the ultrasound image, based on the 3D position of the surgical instruments in the rendered scene. For example, in FIG. 7, ablation needle 745 may be held in the physician's left hand and the needle shaft is to the left of the 3D ultrasound image slice, so that the 2D ultrasound image 705 in the upper right corner of display 720 does not cover any of the 3D features of the needle (or vice-versa). If the needle were held in the physician's right hand, the virtual needle shaft would appear on the right side. To prevent the 2D ultrasound image in the corner of display 720 from covering the needle shaft, the system can automatically move it to a corner that would not otherwise be occupied by graphics or data.

In some embodiments, the system attempts to avoid having the 2D ultrasound image quickly moving among corners of the display in order to avoid overlapping with graphics and data in the display. For example, a function $f$ may be used to determine which corner is most suitable for the 2D ultrasound image to be drawn in. The inputs to $f$ may include the locations, in the screen coordinate system, of the displayed needle tip, the corners of the 3D ultrasound image, etc. In some embodiments, $f$'s output for any given point in time is independent of $f$'s output in the previous frames, which may cause the ultrasound image to move among corners of the display rapidly. In some embodiments, the image guidance system will filter $f$'s output over time. For example, the output of a filter g, for any given frame, could be the corner which has been output by $f$ the most number of times over the last n frames, possibly weighting the most recent values for $f$ most heavily. The output of the filter g may be used to determine in which corner of display 720 to display the 2D ultrasound image and the temporal filtering provided by g may allow the 2D ultrasound image display to move more smoothly among the corners of the display 720.

In some embodiments, other appropriate virtual information can be overlaid on the 2D ultrasound image as well. Examples include: an indication of the distance between the needle's tip and the point in the plane of the ultrasound image that is closest to the needle tip; the cross section or outline of the ablation volume that intersects with the ultrasound slice; and/or the intersection point, box, outline, etc. between the needle's axis and the ultrasound image plane.

Representing Spatial Relationships

At times, when three dimensional relationships are depicted in 2D, or even in 3D, it may be difficult to gauge the relative positions, orientations, and distances among various objects. Consider FIG. 7, in which an ablation needle is shown intersecting an ultrasound image. Depending on the embodiment, it may be difficult to determine the relative angle of the ablation needle and the ultrasound image as well as the distances of various portions of the image to the ablation needle.

In some embodiments, the image guidance system may indicate spatial relationships with graphical indicators. For example, in FIGS. 8 and 9, graphical indicators help indicate the spatial relationship between a needle and an ultrasound image. These also provide an indication of the relative angle of the needle and the image.

In some unpictured embodiments, the image guidance system may draw "guidance graphics" in the form of projective lines between the needle and the ultrasound slice. These lines may be perpendicular to the plane of the slice and serve to indicate the most likely location in the slice where the needle will become visible if it is moved to become coplanar with the slice. Together with stereoscopic head-tracked visualization, the projective lines help a physician determine a more accurate assessment of the location of the needle with respect to the ultrasound slice.

Returning to FIGS. 8 and 9, in some embodiments, uniform-thickness lines between virtual needle and slice plane may be displayed on display 820 and 920. The lines may represent the spatial relationship with three-dimensional rectangular (or any shape) needle projection bars. In various embodiments, the projection bars may be drawn perpendicular to the image, and in such a way that their small edges are aligned with (or parallel to) either the vertical (FIG. 8) or the horizontal (FIG. 9) margins of the ultrasound slice. In some embodiments, the screen-space size of the projection bars may be variable (e.g., distance-dependent) due to perspective. Thus they may provide depth cues for the physician. Further, the staircase appearance of the bars' end edges at the plane of the slice may be a further visual cue for the orientation of the needle with respect to the slice.

Figure 10:
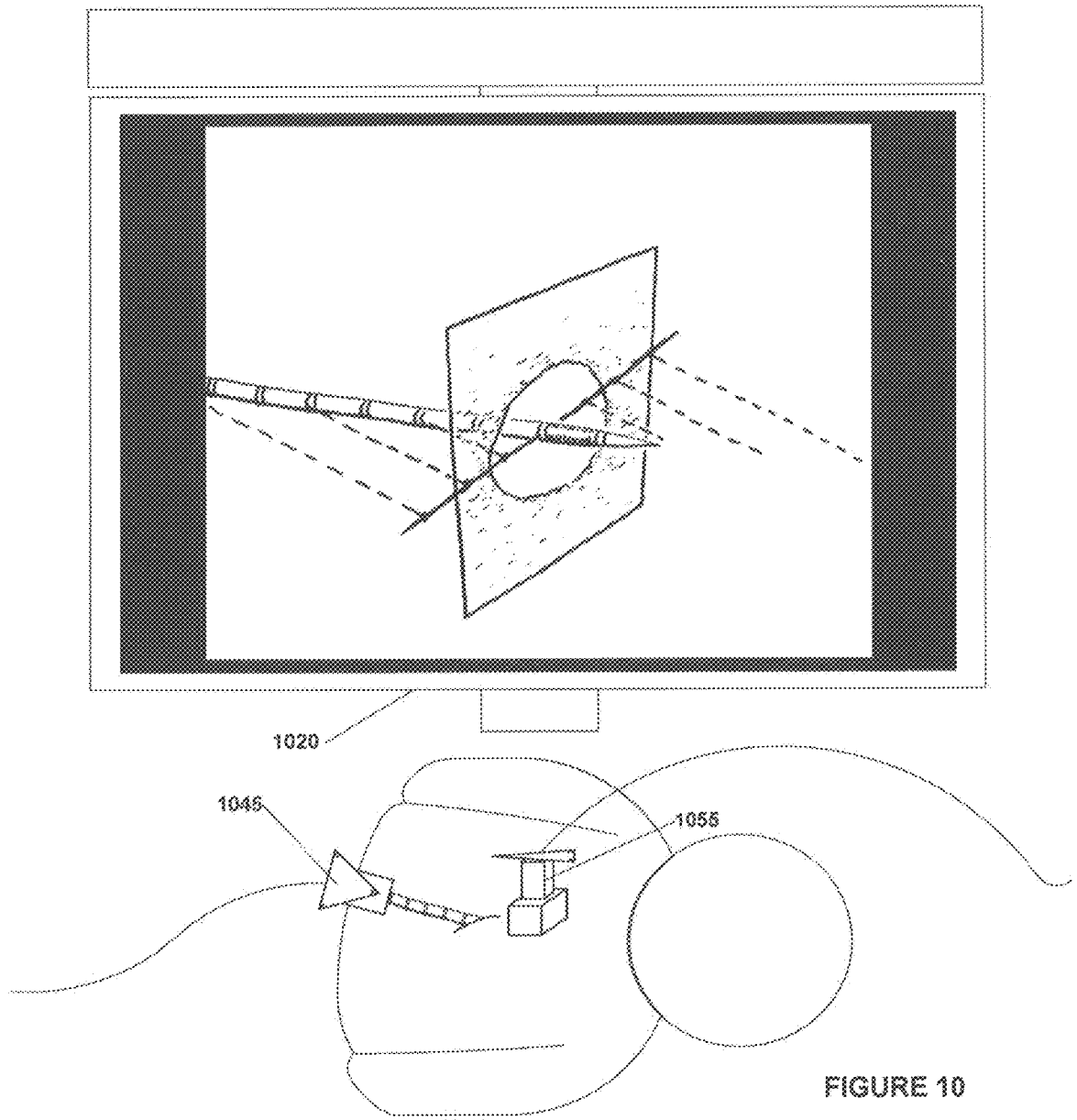
FIG. 10 illustrates a seventh example of displaying image guidance data.

In some embodiments, when the needle is nearly perpendicular to the ultrasound image, the projection bars may appear similar to the needle itself. Therefore, in some embodiments, the rectangular projection bars may not be displayed when the needle is nearly perpendicular to the ultrasound image plane. Instead no projection information may be displayed or project lines may be displayed as dotted or dashed lines. The display of projection lines is illustrated in FIG. 10. In some embodiments, as depicted in FIG. 10, a line may also be drawn that is a projection of the needle onto the image plane of the ultrasound image. This may provide relative orientation information to the user or physician.

Reducing Stereo Display Artifacts With Object Choice

Stereoscopic displays separate the imagery shown to the user's eyes in various ways. Cathode Ray Tube (CRT) based devices, may use temporal sequencing, showing imagery for the left and right eye in temporal sequential alternation. This method may also be used by newer, projection-based devices, as well as by 120-Hz-switchable liquid crystal display (LCD) devices. Another type of stereoscopic display uses spatial separation such as alternating rows (AR) or alternating columns (AC). Example AR displays include the Miracube G240S, as well as Zalman Trimon Monitors. AC displays include devices manufactured by Sharp, as well as many "auto-stereoscopic" displays (e.g., Philips).

Both AR and AC monitors have reduced (often by at least 50%) resolution in one dimension: vertical for AR and horizontal for AC. As a result, some elements—most of all thin lines—when displayed as nearly horizontal AR units and nearly vertical on AC units often feature noticeable artifacts such as aliasing and discontinuities (e.g., a continuous near-horizontal line may appear dashed on an AR display). These artifacts may have a negative impact on stereoscopic fusion (e.g., the human brain's ability to merge the separate left and right eye images into a single 3D mental representation).

Stereoscopic fusion may be useful for improved perception and needle guidance by a physician. In some embodiments, an image guidance system, such as system 300 in FIG. 3A or FIG. 3B, may use thicker lines, particularly in the horizontal, and use fewer near-horizontal lines, borders, and structures when using AR displays. In some embodiments, when using an AC display, the image guidance system may use thicker lines, particularly in the vertical, and fewer near-vertical lines and structures.

Figure 8:
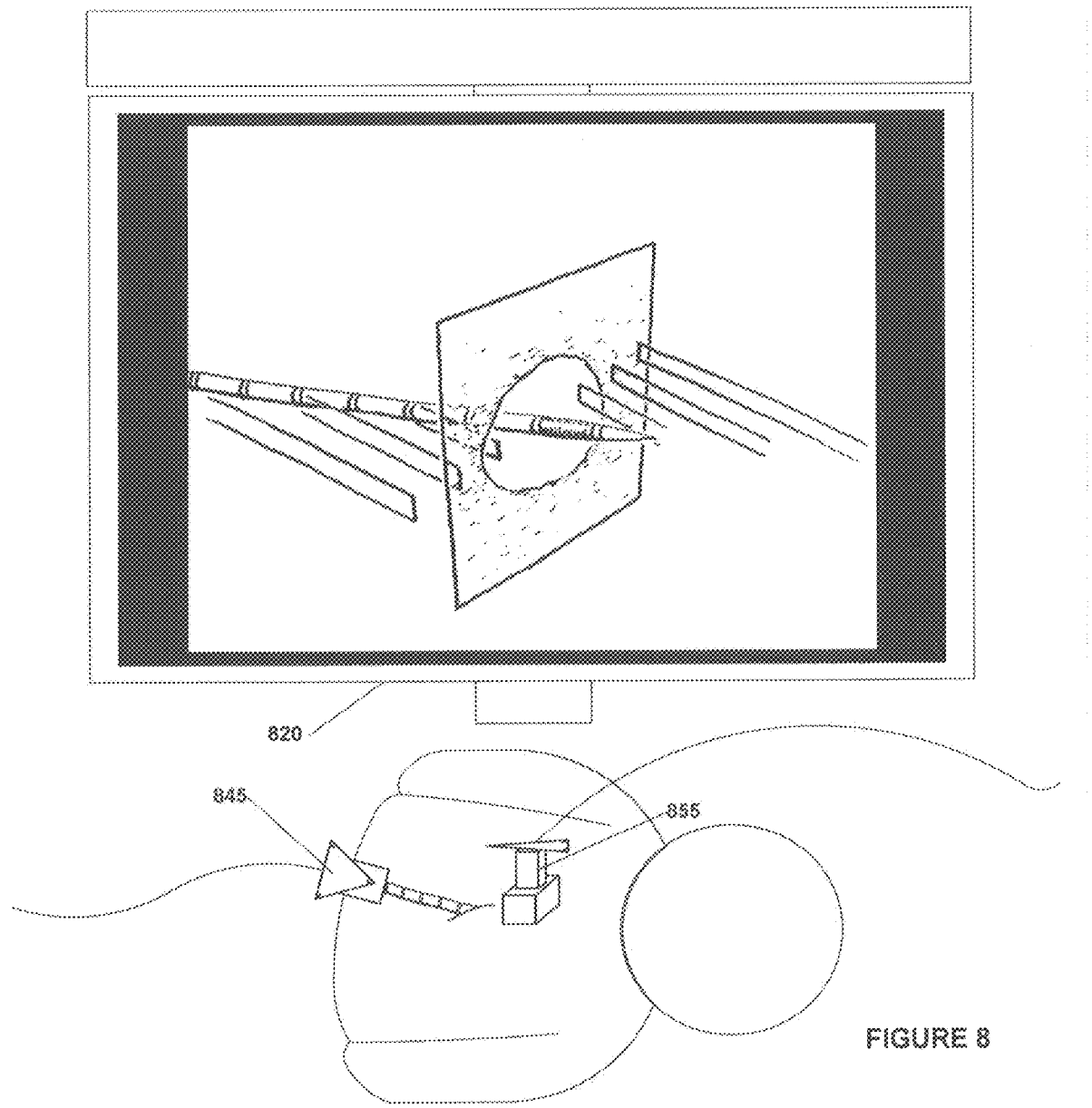
FIG. 8 illustrates a fifth example of displaying image guidance data.
Figure 9:
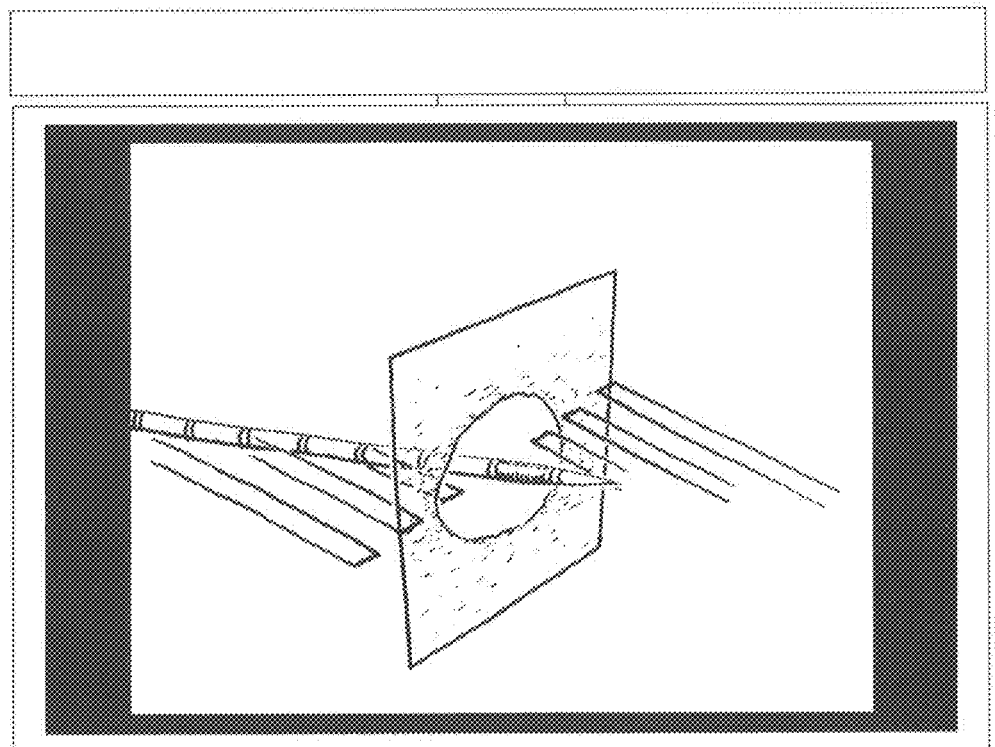
FIG. 9 illustrates a sixth example of displaying image guidance data.
Figure 9:
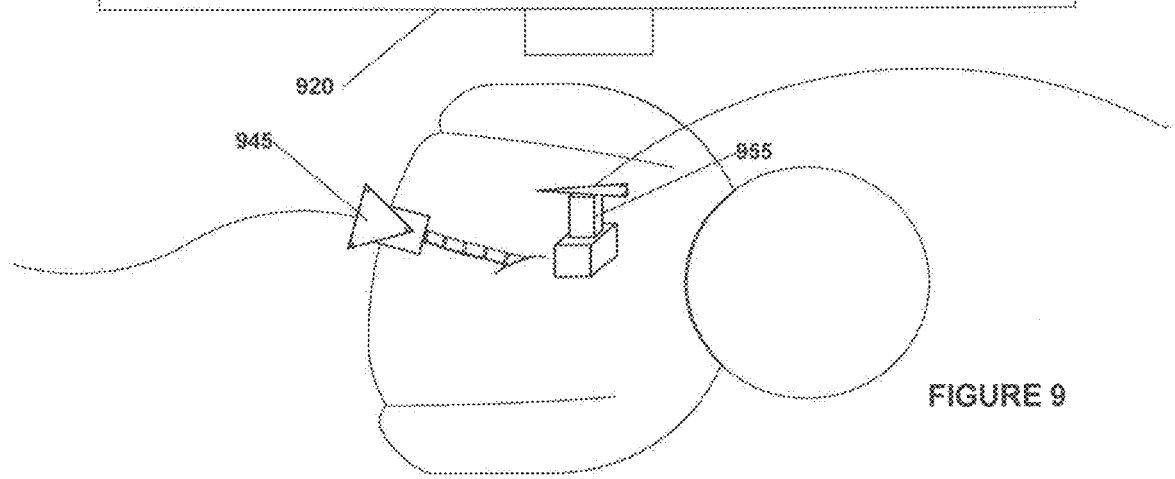

In some embodiments, the projection markings such as rectangular bars shown in FIGS. 8 and 9 are chosen in part based on the type of display being used. Representing the projections in thicker form, such as rectangular bars may help overcome the limitations of AR and AC displays. Further, in some embodiments, the projection bars can be oriented along their long axes (e.g., axes that are perpendicular to the slice) such that in the case of an AR display their short end edges are aligned with the vertical edge of the ultrasound slice and thus will appear mostly vertical in the stereoscopic image. This is illustrated in FIG. 8. For AC displays, in some embodiments, the bars are oriented such that their ends are parallel to the top and bottom of the ultrasound slice and thus are more likely to appear near-horizontal in the stereoscopic image. This is depicted in FIG. 9. The projective bars were used here as an example, but this technique can be applied to any display element in order to accommodate AR or AC displays. For example, if needle drive projections are displayed in an embodiment, such as that depicted in FIG. 6, then the shape chosen to indicate the projected needle drive may be adapted (by showing spheres instead of circles, e.g., or by expanding the width of the drive indicators) to take into account that an AR or AC display is being used.

Reducing Stereo Display Ghosting Effects

In some embodiments, stereoscopic displays may suffer a "ghosting" phenomenon, which may be crosstalk between the left and right eye images. Ghosting can affect frame-sequential, AR, or AC displays. Ghosting may be exacerbated when there is a great difference between the colors or brightnesses between the left and right eye imagery shown in a region of the displayed image. Due to the nature of stereoscopic image display, these differences may occur where the (virtual) stereoscopic depth of the 3D scene to be rendered varies from the plane of the display surface.

In some embodiments, the image guidance system modifies the color and brightness of display elements that are in front of or behind the plane of the display (e.g., where the needle and ultrasound image intersect or the plane of the monitor). The image guidance system may shift the rendered color towards a uniform or background color with increasing distance from the display plane. In some embodiments, this may be accomplished by means of the OpenGL "fog" feature, which can "bathe" all displayed geometry in a color whose opacity increases with distance from the display plane. This may vary on a per-pixel basis. The farther the object is behind the display plane, the more it may be blended with the background color. This may also be applied to objects in front of the display plane by reversing the depth or Z coordinates. In some embodiments, ghosting reduction may also be implemented as a fragment shader or other routine or program, running on programmable graphics hardware or a CPU, etc. The input to a fragment program may be the color of the pixel, the color of surrounding pixels and the depth (e.g., Z depth, or the absolute distance to the plane of the monitor). The program may use the first two inputs to compute the contrast in the region local to the current pixel. The program may then reduce the contrast for those high-contrast regions, based on how far they are from the monitor's display plane. This program may also be implemented as the converse or opposite of an edge enhancement filter while also taking into account the screen depth of the edges.

Representing Non-Intersecting Objects or Images

Figure 11:
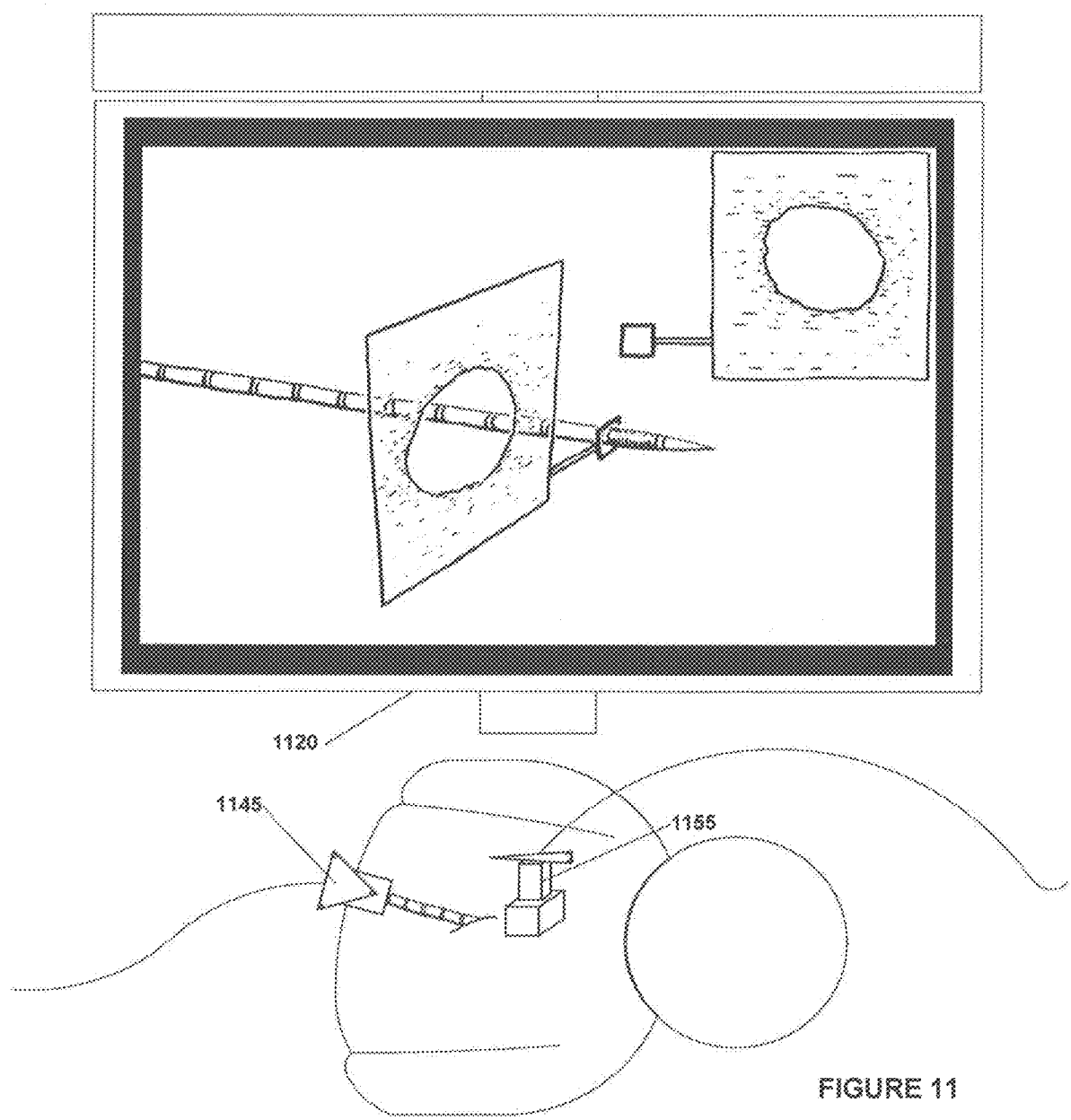
FIG. 11 illustrates an eighth example of displaying image guidance data.
Figure 12:
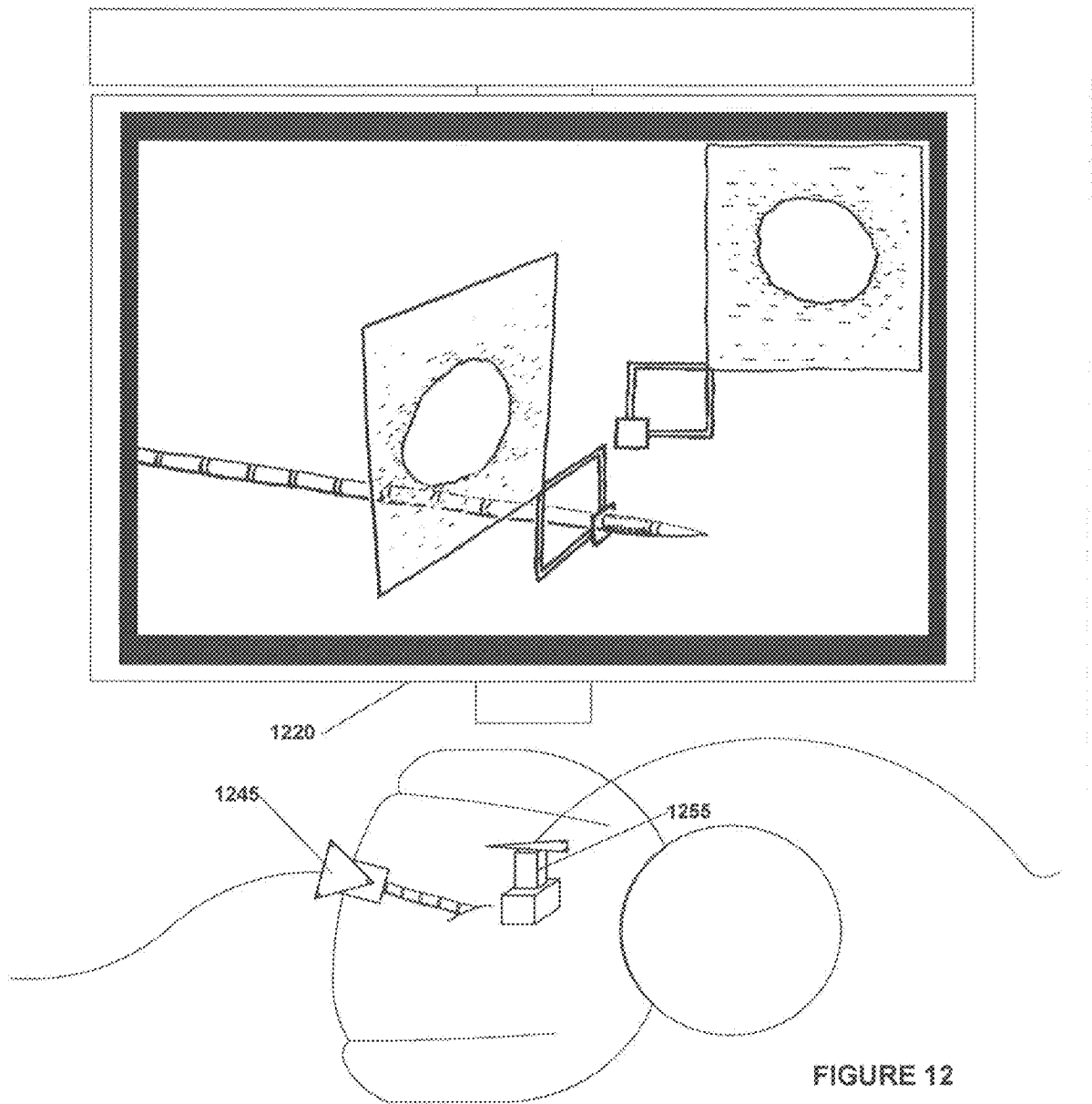
FIG. 12 illustrates a ninth example of displaying image guidance data.

When data related to two devices or surgical instruments are displayed with relative emplacement, it can be difficult to orient their relative locations if they do not intersect. In some embodiments, an image guidance system will render relative location information. The relative location information may be shown with color (e.g., objects may be rendered in brighter colors if they are closer), with rendering techniques (e.g., objects may be rendered with transparency so that one object behind another may be visible, but visually appear behind the closer object), with geometry (e.g., a geometric connector may be shown that will allow the viewer to discern the relative relationships), or with any other appropriate technique. FIGS. 11 and 12 illustrate example geometry and transparency being used to show relative locations of two objects.

For example, in some embodiments, if the intersection point of an ablation needle is outside of the area of the ultrasound slice, the image guidance system can draw geometry, such as a line (or rectangle) in the plane of the slice to indicate the needle's and ultrasound image's relative positions. This is depicted in FIG. 11. In some embodiments, the relative locations could also be represented using vertical and horizontal elements coplanar with the ultrasound or other image slice, as depicted in FIG. 12. In some embodiments, using geometry that is coplanar with the ultrasound image slice may provide an intuitive understanding of the relative locations of an image slice and an ablation needle.

Rendering Techniques for 3D Fusion

In some embodiments, various data displayed by the image guidance unit may be displayed as lines, frames, or 2D objects. For example, the ablation volume of FIG. 5 may be rendered as a wire-frame using 2D lines. Similarly, the projection lines of FIG. 8 may be rendered as 2D lines.

In some embodiments, some or all of the displayed data may be represented in 3D space and rendered as such. For example, the ablation volume of FIG. 5 may be represented using beam-shaped, pipe-like, swept rectangular, 3D polygonal primitives, etc. in order to "build" the wireframe representation. Similarly, the rectangular projection lines of FIG. 8 may optionally be built with beam-shaped, pipe-like, swept rectangular, polygonal solids, etc. For example, the projection lines of FIG. 8 may be flat rectangular prisms, and the ablation volume of FIG. 5 may be represented as thin, curved tubes with a colored stripe pattern. In some embodiments, using 3D objects to represent various data may provide improved 3D fusion for viewers.

Additionally, in some embodiments, a "surface detail" texture may be added to various objects. Adding surface detail may aid with stereo fusion because of the addition of surface texture that may provide stereoscopically "fusible" details (e.g., anchor points) on an object. A simple line or uncolored 2D object may not provide as many anchor points. Examples of possible textures include the use of color stripes or mosaics, metallic textures, and random noise textures. In some embodiments, textures may be selected so that the spatial pattern and frequency does not cause aliasing in the stereoscopic display's alternating scanlines or columns, nor with the checkerboard-interleaved pixels which are used by certain projection-based stereoscopic displays.

In some embodiments, surface shading from one or more light sources is used. Examples of surface shading that may be used includes surface shading from one or more light sources, which may be supported in graphics processor hardware, as well as other enhancements like cast shadows, and cues such as global illumination. Surface shading may contribute to increased depth perception in the guidance image.

Marking Points of Interest

In certain procedures, physicians need to keep track of multiple spots within the volume of the patient or keep track of a single point or feature while looking at other parts of the volume. For example, when a physician is going to perform an ablation, before inserting any needles, the physician will often scan the tissues at the procedures site to find all targets (e.g., tumors) and note other features of the tissues. Then, later in the procedure, the physician may return to the previously identified points-of-interest. For example, a physician might first scan the liver and find seven lesions that she will attempt to ablate. After ablating the first lesion, she must then find the second lesion again, and so forth. Before finishing the procedure, she must verify that she has ablated all seven of the lesions that she identified at the beginning of the procedure. This constant scanning and rescanning can be time consuming and error prone. Further, when if a procedure where the surgeon is attempting to locate, for example, fluid-filled cysts, once a needle pierces the cyst, the fluid may drain out, making the target difficult or impossible to locate again with ultrasound.

Figure 13:
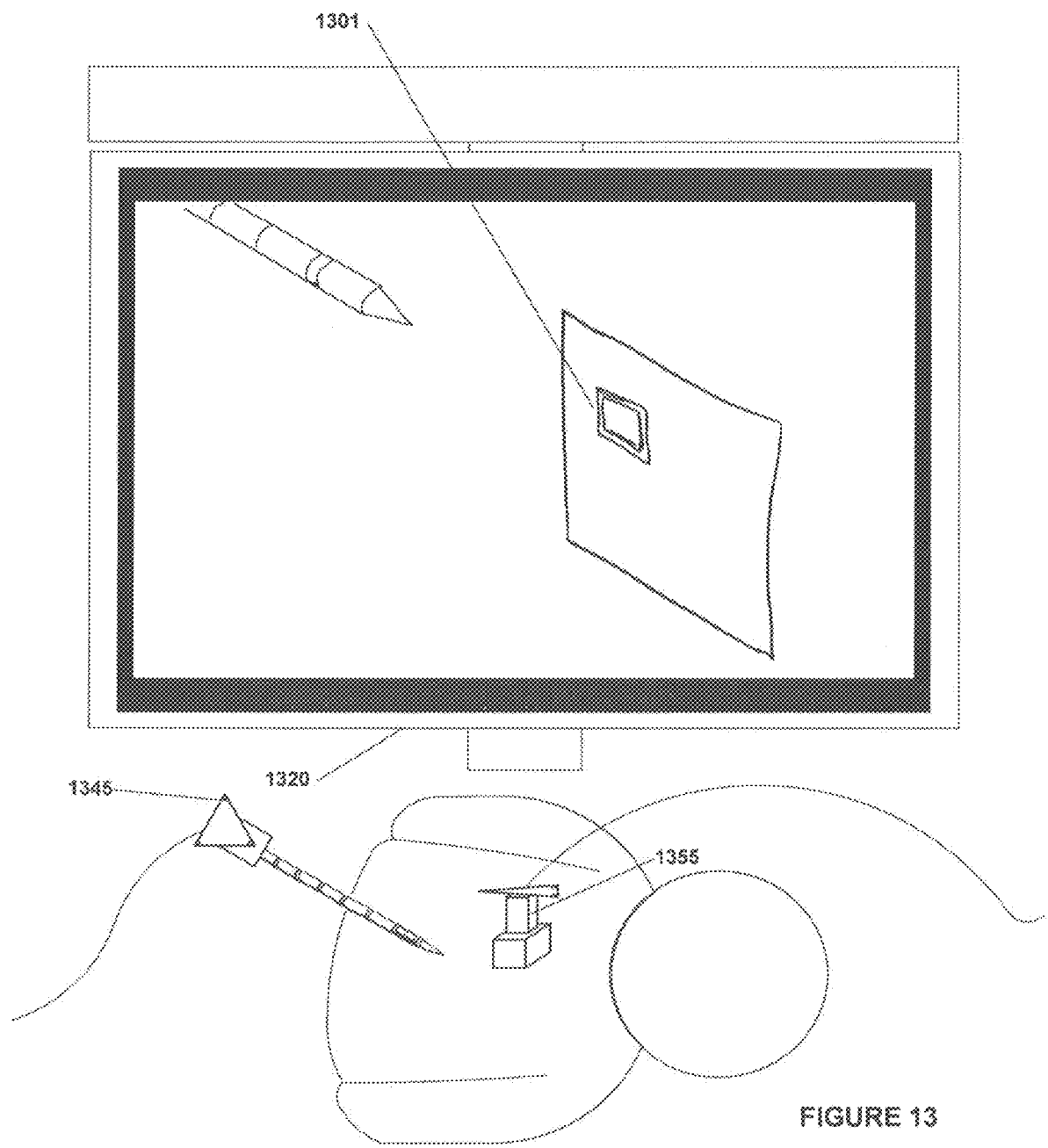
FIG. 13 illustrates a tenth example of displaying image guidance data.
Figure 14:
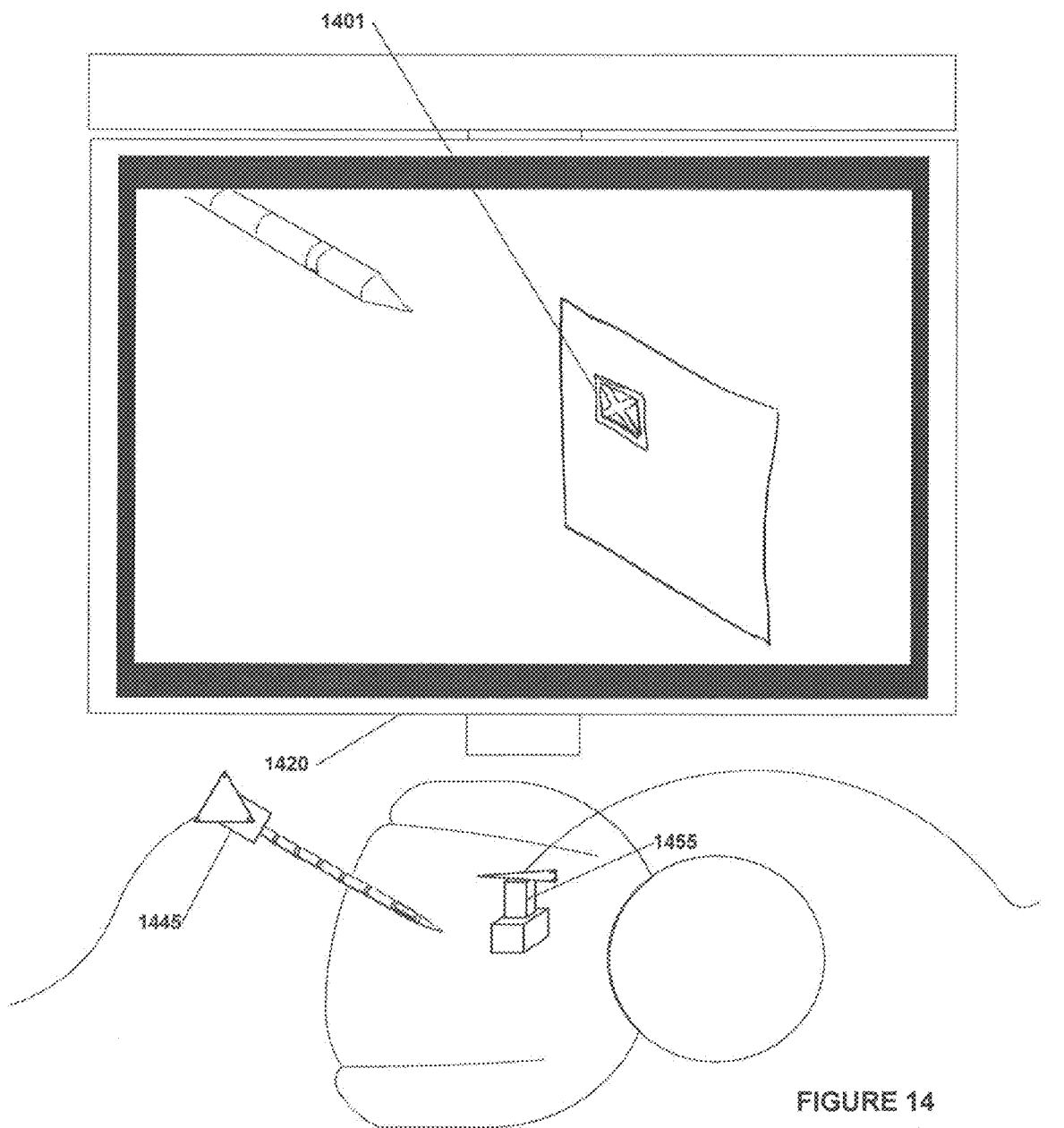
FIG. 14 illustrates an eleventh example of displaying image guidance data.
Figure 15:
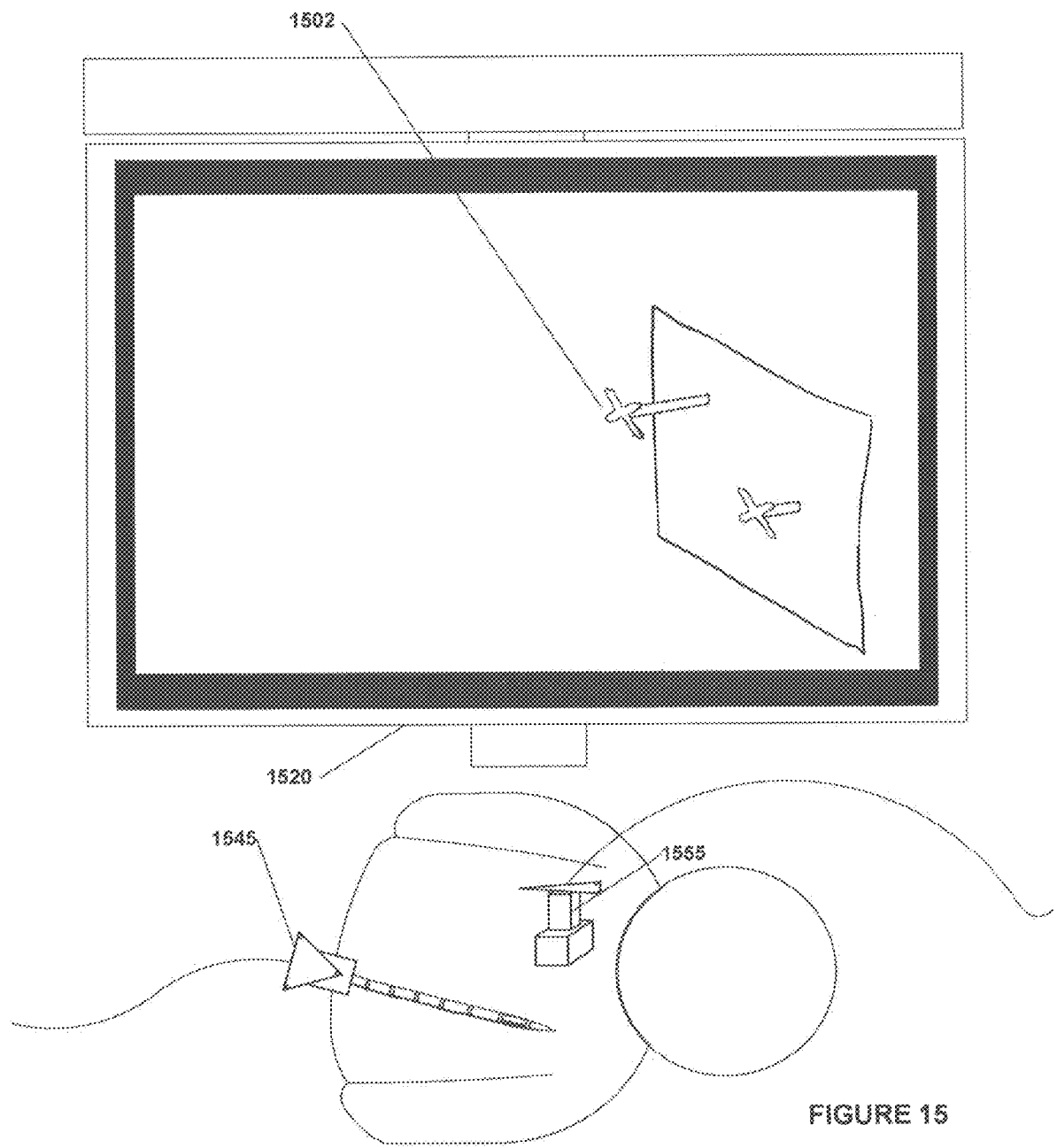
FIG. 15 illustrates a twelfth example of displaying image guidance data.

In some embodiments, the image guidance system may allow the physician to mark or keep track of points or features of interest. In various embodiments, the physician can mark the points or features of interest in various ways. For example, consider a procedure where the doctor is using the image guidance system with an ablation needle and an ultrasound wand. The doctor may be able to mark the point by pressing a button on a keyboard or medical device, by gesturing or issuing a verbal command, or with any other appropriate method. The point of interest may be marked at the point where the needle intersects with the ultrasound image plane, where the needle's projection intersects with the ultrasound image plane, or any other appropriate relationship (such as at the location of the tip of the needle). For example, when the physician identifies a point-of-interest 1301 within the ultrasound image, she can point to it using the needle even if the needle is outside the body of the patient. This is depicted in FIG. 13. The physician (or assistant) may then press, for example, a button or foot pedal, which informs the image guidance system to store the 3D position of this point-of-interest 1301. FIG. 14 illustrates an X being displayed where a point of interest 1401 has been marked. In some embodiments, the system may then display the position of this point-of-interest 1401 relative to the ultrasound plane and the needle. For example, an X-shaped marker 1502 may be displayed on display 1520 to show the relative position of the marked position and the surgical instruments, as depicted in FIG. 15. In some embodiments, the system may also display a bar that connects the X marker 1502 of the point-of-interest to the nearest point (or the point to which a normal vector of the image plane would reach the X), as depicted in FIG. 15. This visually indicates, to the physician, the distance between the ultrasound image and this point-of-interest. Should the physician want to see the point of interest again in the live ultrasound image, the graphics indicate to where she should move the ultrasound transducer to view that point in the ultrasound image. In some embodiments, the image guidance system may also display the numerical distance (e.g., in mm) between the ultrasound image and the point-of-interest (not shown).

Physicians, during some liver ablation procedures, may manage fifteen points-of-interest, or even more. As depicted in FIG. 15, in some embodiments, there may also be multiple markers 1502 of point of interest simultaneously displayed. The image guidance system may be able to store and display any number of points of interest simultaneously. If there is more than one point-of-interest in view, the image guidance system may display a number next to each one (not pictured). In some embodiments, in order to reduce visual clutter if there are many points of interest, those points which are closer to the ultrasound image plane are drawn more saliently or vividly (with more bold color and thicker lines) while the points that are far away are drawn less saliently (more transparent, blurred, muted colors, etc.). Additionally, in various embodiments, other representations other than an X (such as a point, point cloud, sphere, box, etc.) may be used and multiple markers or locations may be represented with different markings.

In some embodiments, the image guidance system stores the points-of-interests' positions in the position sensing system's coordinate system. If the position sensing system is fixed to the image guidance system, then, if the patient or image guidance system are moved, stored points-of-interest may become incorrectly located. In some embodiments, this can be remedied via a fiducial or other detectable feature or item, the pose of which relative to the tracking system may be continually, continuously, periodically, or occasionally measured. The fiducial may be attached to the operating table, the patient's skin, or even embedded into the tissue itself (e.g., as a magnetic tracking coil), and the points-of-interest' positions, relative to it, can be stored and displayed. For example, in a system where magnetic tracking is used, a magnetic tracking coil may be affixed to the operating table or patient.

Data Visualization Processes and Data

Displaying Volumetric Data

Figure 1:
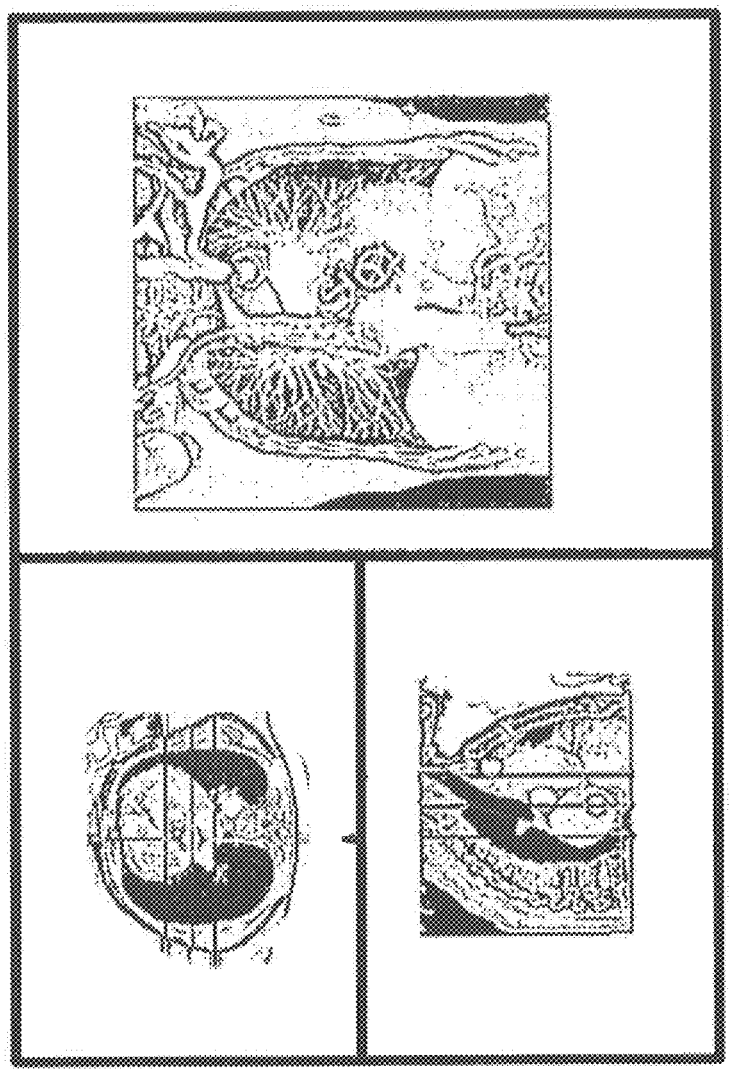
FIG. 1 illustrates the display of 3D volumetric data as planar data along three axes.

There are numerous types of volumetric or 3D data that various embodiments of the image guidance system herein may display. Such data may include CT scans, MRI, PET, 3D ultrasound, and any of numerous other types of 3D data. In some embodiments, in order to display 3D data on a 2D interface, such as a computer screen, or even a 3D interface, such as a head-mounted display or other 3D display, a subset of the data is chosen to display. This subset of data can include axis-aligned slices, the entire volume, or a sub-volume of the data. An inherent difficulty with image guidance is the display of three dimensions of data on a two dimensional screen or "dual eye" three dimensional display. When displaying 3D data, such as CT scans, a system might only display a single plane, or show three orthogonal planes separately on the screen, as shown in FIG. 1. The data may also be shown as a volumetric 'block' of data, as shown in FIG. 2.

Figure 2:
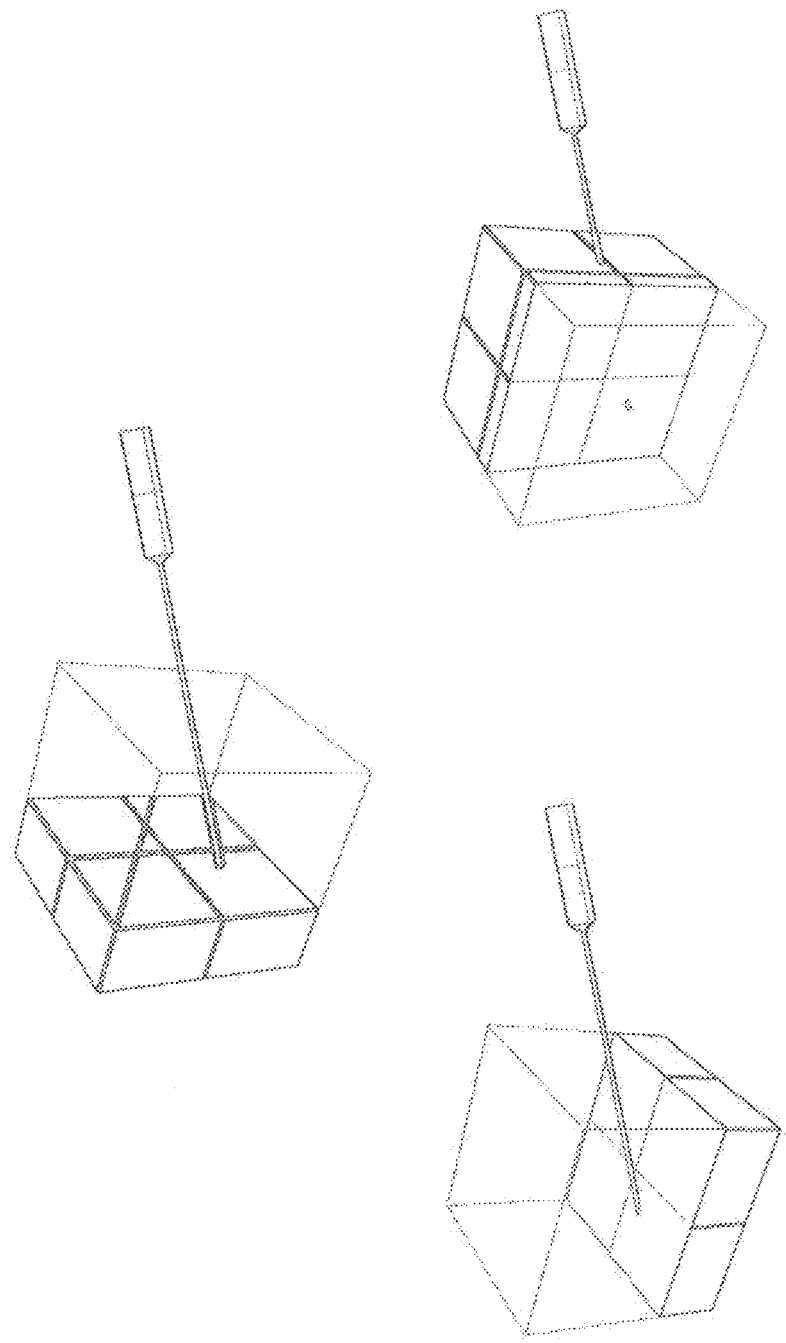
FIG. 2 illustrates the display of 3D volumetric data as a 3D block of data.

Therefore, as depicted in FIG. 2, if a sub-volume is displayed, the outer surface of the volume may be displayed as a box on the screen and the data interior to the rendered box may not be visible to the doctor. The 3D data may be displayed in correspondence to the surgical instrument that the doctor is holding (e.g., note the needle and 3D data interacting in FIG. 2). The 3D data may also be displayed as axis-aligned slices, as shown in FIG. 1. In previous systems, when the doctor wanted a different view of the 3D data (either a different volume, as in FIG. 2, or different set of images, as in FIG. 1), she would have to alter the location of the displayed planes, using, for example, a cursor (controlled by a mouse or trackball).

Figure 16:
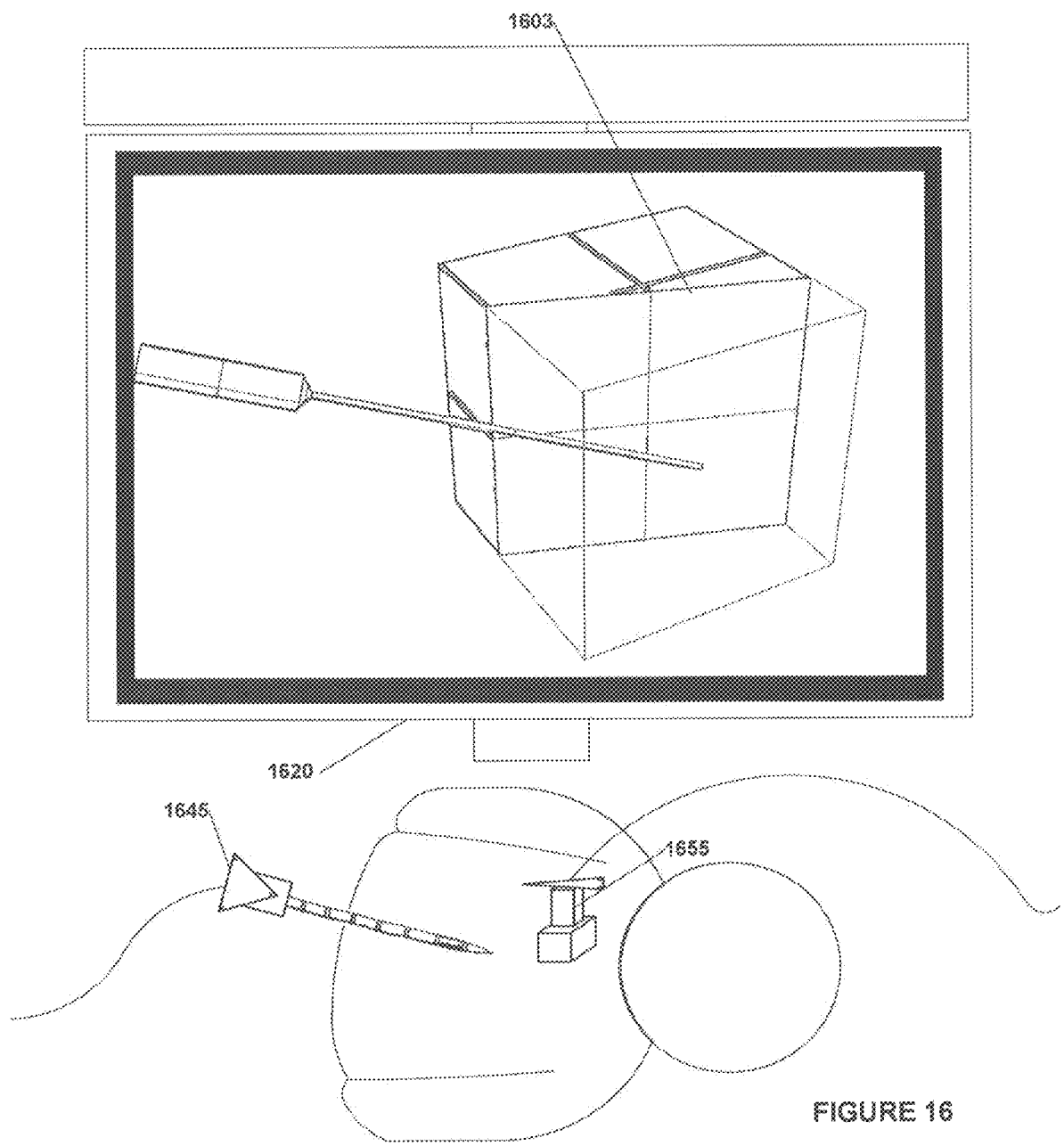
FIG. 16 illustrates a thirteenth example of displaying image guidance data.

In some embodiments, the image guidance system controls the display of the 3D data with a medical device. For example, as depicted in FIG. 16, one of the planes 1603 of the 3D data displayed on display 1620 may be aligned with a tracked surgical needle, such as surgical needle 1645. Additionally, in some embodiments, separate data related to another medical device, such as ultrasound data, may be displayed on display 1620 (not shown). This data may be obtained, and its pose or emplacement known, based on a tracked ultrasound wand, such as tracked ultrasound wand 1655 of FIG. 16.

In some embodiments, the displayed plane 1603 of the 3D data may be axis-aligned in one direction and controlled by the surgical instrument in the other two directions. This may result in an image such as that displayed in FIG. 16, where the image is aligned with the, or Y axis, and the location in the X and Y axes is controlled by the needle placement. The plane of orientation of the surface may also be chosen based on alignment with the plane of the display (choose the closest plane to the screen's plane); closest to one of the three traditional orthogonal planes (sagittal, transverse, coronal); or one specified by the physician (or an assistant who is not in the sterile field), using a control knob, lever, or foot pedal. If the needle is curved (or bent into a curve from the pressures acting on it by the tissues and the physician's hand), the system may choose the plane that most clearly displays the curvature of the needle.

Figure 17:
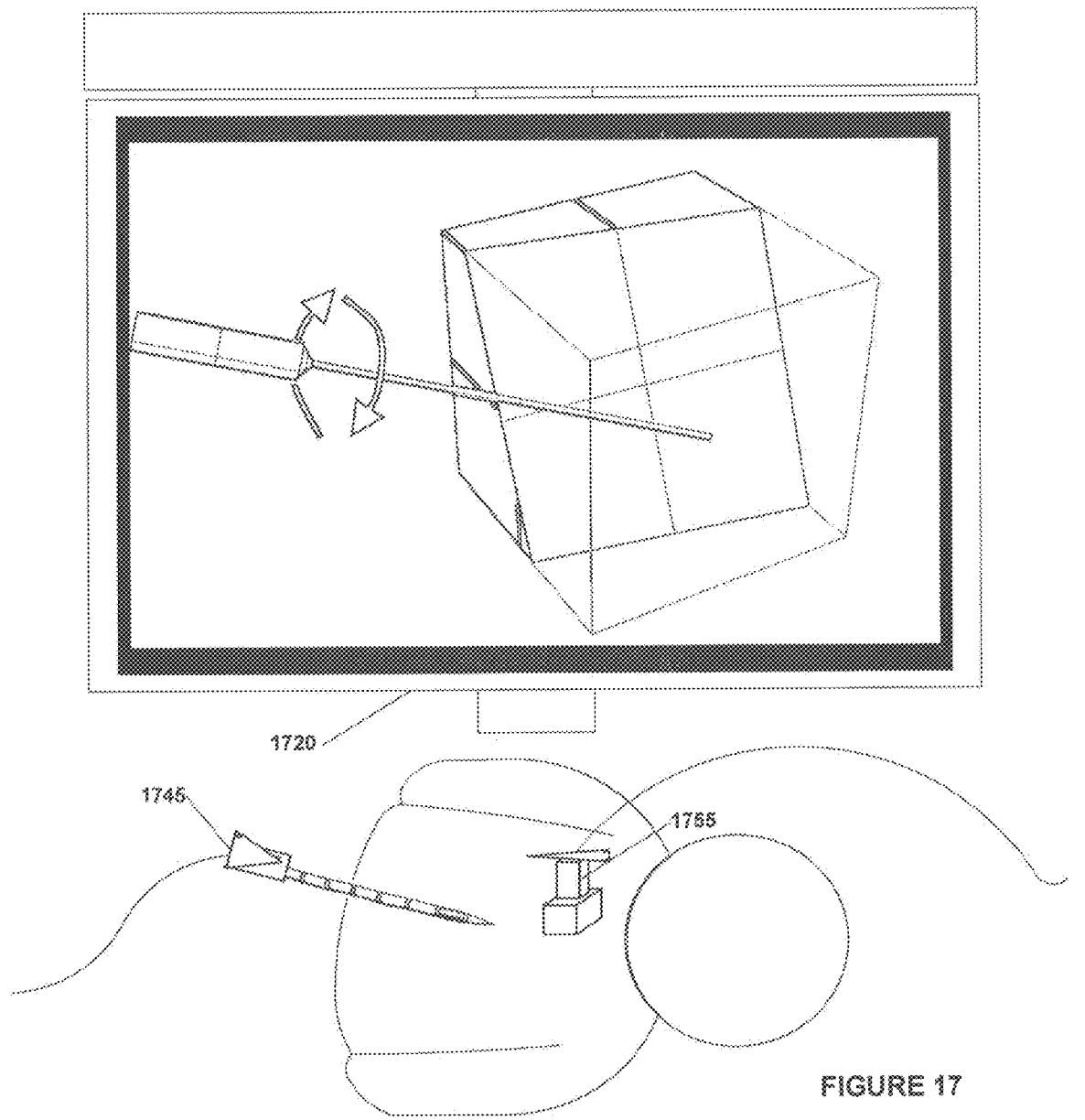
FIG. 17 illustrates a fourteenth example of displaying image guidance data.

In some embodiments, the display plane may also be controlled by the rotation of the medical device. This is depicted in FIG. 17, which illustrates that, once the needle 1745 is rotated, the display plane for the volumetric data is rotated and shown in display 1720. In some embodiments, the image guidance system may choose a plane that intersects some feature or landmark on the needle's handle (such as the port where the wire exits, or a molded ridge) or the needle's shaft (such as the openings in the shaft from which the paddles deploy on the needles made by RFA Medical™). Then, when the physician physically twists the needle, it has the effect of rotating the cross-sectional plane (FIG. 4). This may allow a physician to intuitively specify its orientation by using the needle. The rotational arrows in FIG. 17, in various embodiments, may or may not be shown on display 1720.

The system can work with static or real-time (or near real-time) volumetric data. In some embodiments, the system may display a cross section of the volumetric image along a plane that intersects the axis of a surgical needle or other surgical or medical device. The system may continually update the position and orientation of the cross-sectional plane as the physician moves the needle. If the volumetric or 3D image data is from a real-time imager, such as a 3D ultrasound transducer, then instead of having to continually manipulate both the needle and transducer, the physician may place the transducer such that the ultrasound volume includes the target, and then to leave the transducer stationary. She then can manipulate the needle's position, before it pierces the tissues, until the target tissue appears visible in the slice controlled by the needle.

Physicians often attempt to maintain 2D ultrasound planes in order to keep the shaft of the needle within the ultrasound image. Doing so may allow then to watch as the needle advances through the tissues. In some embodiments herein, the image guidance system may maintain the displayed ultrasound image within the needle's path automatically. If the doctor can see what is in the needle's path (as shown in the displayed plane of the 3D volumetric data) she may be able to see what will be in the needle's path when she drives the needle. By being able to see this, she may be able to avoid piercing any tissue that should not be pierced by the needle's path. In some embodiments, as the physician advances the needle towards a target, the cross-sectional plane may be chosen automatically by the image guidance system such that it shows the needle, the tissue surrounding the needle, and any structures that are about to be pierced by the needle.

In some embodiments, similar techniques can be used to control the images that are displayed in 2D, as in FIG. 1. That is, the manipulation of a medical device, such as a needle, scalpel, ultrasound wand, etc, can control what planes are shown in the display. For example, if a surgeon moved a needle toward and away from herself, she might sweep through the 3D volume and the corresponding slices of the 3D volume may be shown on the display.

As noted above, various embodiments use live or real-time volumetric images (e.g., intraoperative 3D ultrasound), static volumetric images (e.g., pre-operative CT or MRI) or hybrid volumetric images (e.g., pre-operative CT images that are continuously warped to be in registration with live 2D ultrasound or fluoroscopic images, or laser-scanned 3D point sets representing the surface of tissue).

Visualizing Portions of Volumetric Data

When displaying 3D volumetric data, voxels in front (closer to the virtual camera) typically obscure the voxels behind them. This hides information that may be important from preoperative 3D data and real-time or live 3D data because the surgeon can only clearly view the closest voxels. As noted above, one way to deal with displaying volumetric data is to allow the doctor to view the data as 2D slices, in cross section, etc. In some instances, however, there are determinable differences among the voxels in the 3D data. Therefore, in some embodiments, the image guidance system can display only those voxels that meet certain criteria. For example, in the case of a preoperative CT scan, the voxels containing bone matter should be determinable based on tissue density. Therefore, the image guidance system may display only those voxels within a certain range of tissue densities. As another example, when the volumetric image of a fetus in the womb is visualized from 3D ultrasound data, embodiments of the image guidance system may make all voxels that represent fluid surrounding the fetus transparent or invisible, thus allowing the surface of the fetus to be visible.

Some types of 3D imaging data can provide flow information. In some embodiments, the image guidance system can be set to only display only those voxels that contain flow information. For example, some ultrasound scanners, including 3D ultrasound scanners, can measure motion and flow within the imaged area using Doppler techniques. The portions of the image that have flow above some threshold velocity may be displayed using a particular color or a gradient of colors determined based on the flow information. The remainder, non-flowing part of the ultrasound image may be drawn as traditional grayscale, or may be made invisible.

Figure 18:
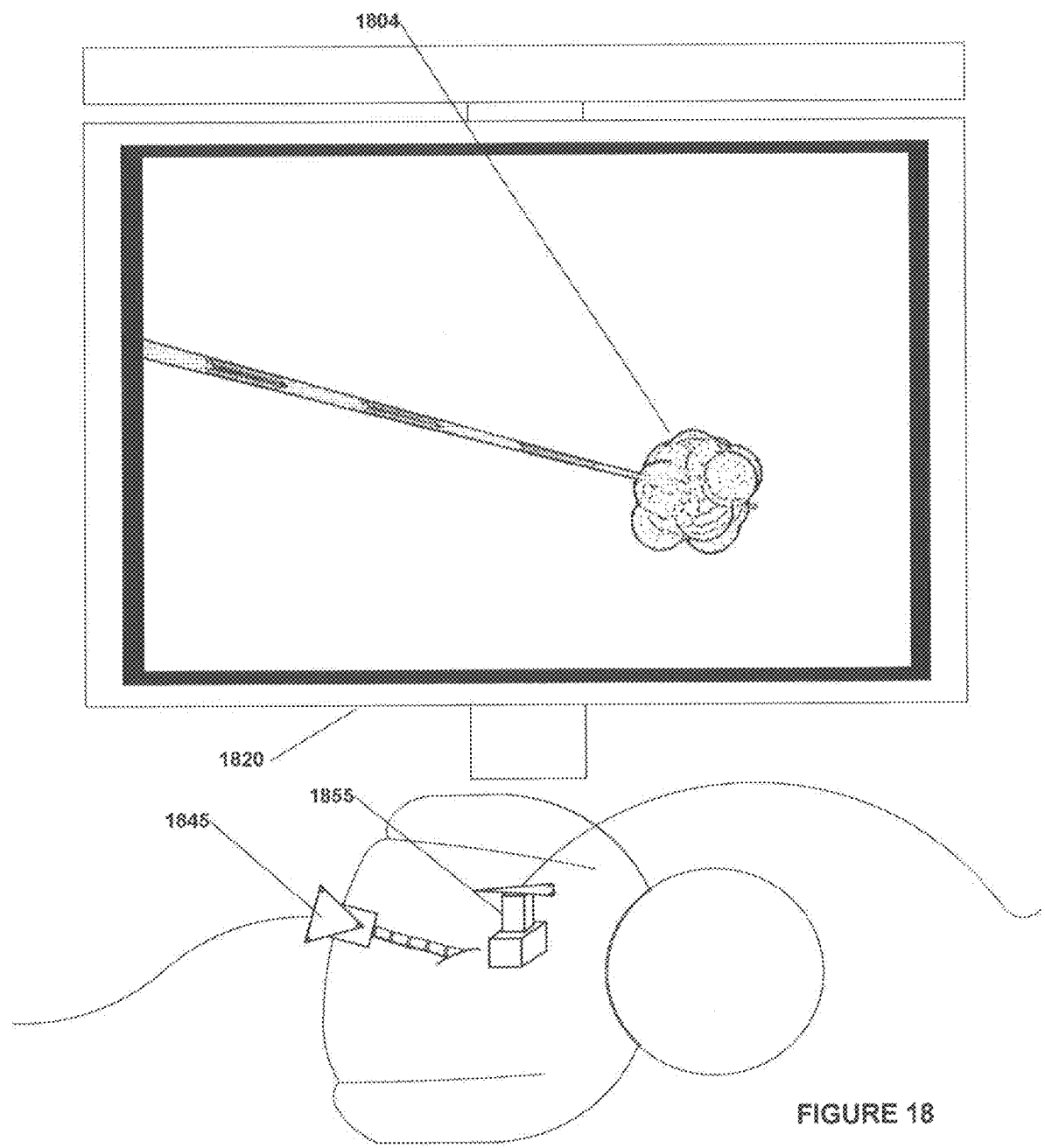
FIG. 18 illustrates a fifteenth example of displaying image guidance data.

For example, in some embodiments, the image guidance system may have a Doppler 3D mode, in which volumetric images (such as a 3D ultrasound) are sampled, and then those volumetric images are displayed such that only those voxels which contain flow (above some threshold velocity) are opaque, while all other voxels (without sufficient flow) are made transparent. By displaying only the portions of the image that have Doppler-detected motion, the image guidance system may provide an easy-to-decipher 3D image of the progress of the ablation. For example, FIG. 18 illustrates a needle 1845 ablating tissue while a 3D ultrasound wand 1855 is collecting ultrasound data. The Doppler data is collected from 3D ultrasound wand 1855 and only the progress of the ablation 1804 is shown on display 1820. One or more slices of the collected ultrasound data may also be shown on display 1820 (not pictured).

Figure 19:
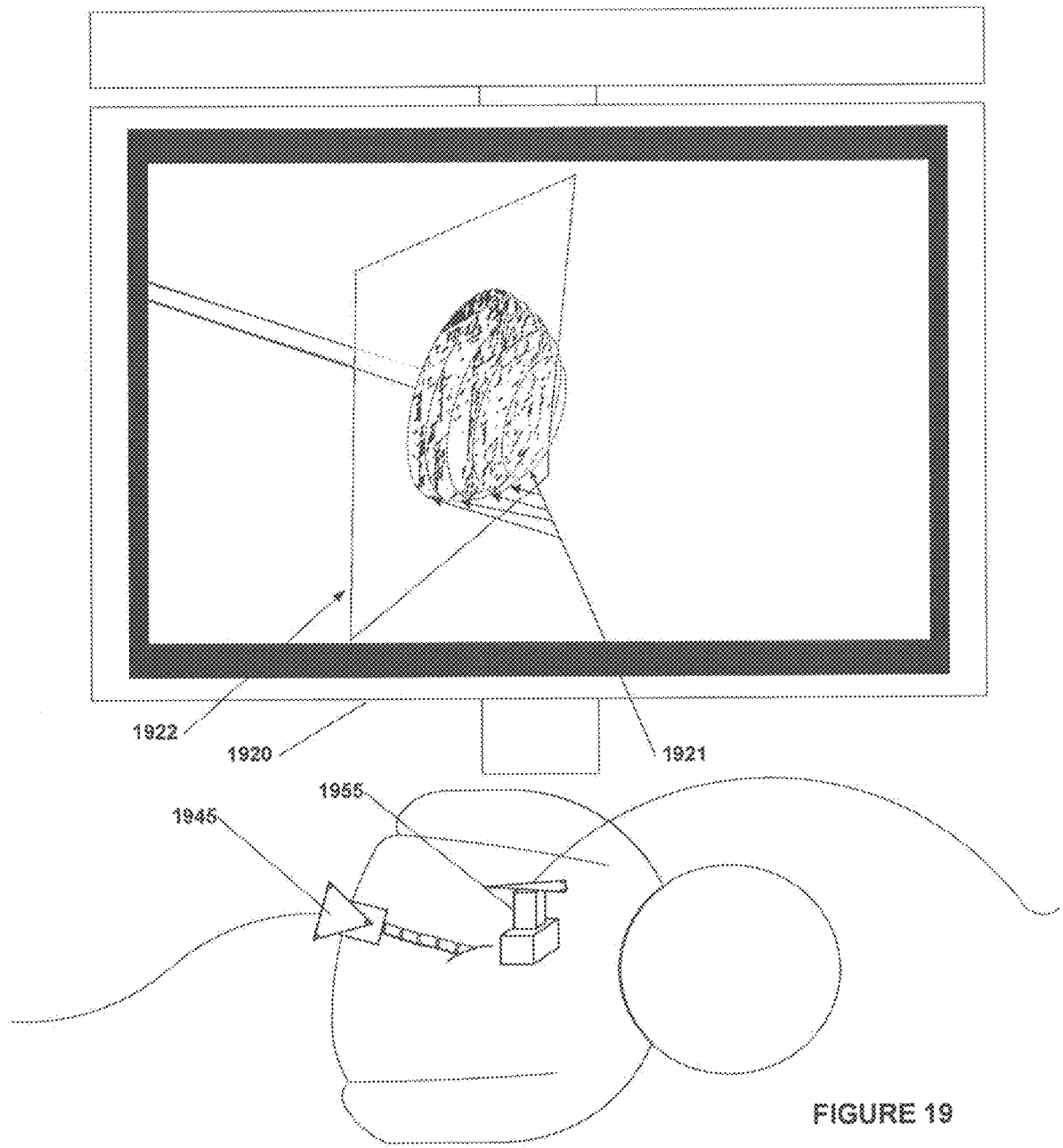
FIG. 19 illustrates a sixteenth example of displaying image guidance data.

In some embodiments, Doppler information can be collected over time as the doctor sweeps a 2D ultrasound wand over a volume. Since the ultrasound wand is tracked, the image guidance system can determine the relative locations of the collected ultrasound slices and locate them in 3D space. From this data, in some embodiments, the image guidance data can approximate 3D flow information in various ways. For example, in some embodiments, in order to observe the progression of the ablation with a 2D transducer, the physician may continually sweep the ultrasound transducer back and forth over the general area of tissue that contains the lesion and ablation needle. Some of the tissue being ablated contains may expand into micro bubbles that can be detected in ultrasound. The image guidance system may extract those pixels and represent the area of Doppler flow (e.g., "a Doppler slice"), relative to the latest 2D ultrasound image ("the ultrasound slice"). For example, as depicted in FIG. 19, as 2D ultrasound wand 1955 is swept across the volume of interest, Doppler slices 1921 may be collected and displayed on display 1920. Additionally, the ultrasound slice 1922 may also be displayed. Optionally, ultrasound needle 1945 may also be displayed on display 1920.

In some embodiments, older Doppler slices may be drawn more transparently, with more blur, in order to reflect that, the older a slice is, the more out-of-date its image contents have become. Eventually, every sampled slice may become completely invisible, no longer being presented to the user. This prevents out-of-date images from obscuring the view of more recent images.

In some embodiments, the ultrasound slices are rendered using various techniques. For example, they might be rendered using a technique from Garrett et al., *Real-Time Incremental Visualization of Dynamic Ultrasound Volumes Using Parallel BSP Trees*. Proc. IEEE Visualization '96 (San Francisco, Calif., Oct. 27-Nov. 1, 1996), pp. 235-240, 490, which is hereby incorporated by reference for all purposes. For example, each rendering frame, a binary spatial partition (BSP) tree data structure may be used to compute a back-to-front ordering of each slice. Then the slices may then be rendered in back-to-front order, such that the transparency and occlusion are handled correctly. Reconstruct, in 3D, only the portions of the image that have Doppler-detected motion may make the 3D images easier for the physician to decipher, thereby improving her understanding of the progression of the ablation.

In some embodiments, a rendering technique is used to sort Doppler slices using the depth of the center-point of each Doppler slice. This technique may result in an approximate back-to-front ordering as the slices may intersect. In some embodiments, a BSP tree algorithm may split one slice into two in the case where they intersect each other. Since sorting by the slices' center point depths results in an approximate ordering, the resulting rendering may have some visual artifacts (e.g., pieces of one slice that should appear to be behind another slice, but instead appear in front of it). To minimize the presence of these artifacts, in some embodiments, the image guidance system may render the Doppler slices in two separate passes. In the first pass, a clipping plane, co-incident with the most recent ultrasound slice, is employed to discard the portions of any Doppler slices that are in front of the ultrasound slice. Then the ultrasound slice is drawn, followed by the second pass of the Doppler slices. This second time, the clipping plane discards the portions of any Doppler slices that lie behind the ultrasound slice.

Thin Visualization of 3D Data

As noted above, in traditional rendering of 3D volumetric data, data or voxels in the front of the rendered image may occlude data or voxels towards the back of the volume. This may be a problem when the data that is further back from the surface is the information that a physician needs to see. Various techniques for overcoming this are given above. More techniques are given in this section.

In some embodiments, the 3D volume data herein may be rendered with a "thin" field of view or depth of focus. For example, in some embodiments, the image guidance system renders a single plane-of-interest in sharp focus, while rendering the rest of the volume dataset, in perspective projection, as transparent and blurry, with stereo cues and/or motion parallax, and spatially registered to the plane-of-interest. This provides the user some context and representation for features located outside of the plane-of-interest, while minimizing their visual interference with image features in the plane-of-interest. In some embodiments, a thin volume of interest (as opposed to a plane of interest) may also be rendered. The volume of interest may include a small and/or user-controllable slice of data that is rendered in sharp focus with, as above, the rest of the volumetric data (in front of and behind) the thin volume of interest rendered in a blurry, transparent, or other technique.

This thin depth-of-field volume visualization may have several medical applications. It may be useful to help the physician/user guide a needle towards a target located in the plane-of-interest, while simultaneously avoiding features in front of or behind the plane-of-interest. It may also be used to identify and mark features (e.g., points, organ boundaries, tumors) in the volumetric images (described above). These tasks can be performed with real-time volumetric images (e.g., intraoperative 3D ultrasound), static volumetric images (pre-operative CT, MRI, etc.) or hybrid volumetric images (e.g., pre-operative CT images that are continuously warped to be in registration with live 2D ultrasound or fluoroscopic images, or laser-scanned 3D point sets representing the surface of tissue).

Further, this technique can be combined with other techniques herein. For example, in order to control the plane or volume of interest (location, orientation), a surgeon may manipulate the needle as described above. In some embodiments, the plane or volume of interest may be parallel and coincident with the screen-planet, or it may have some other spatial relationship to the surface of the display screen. For example, the plane or volume of interest may contain the needle that the physician is placing into the tissue. In some embodiments, the doctor or other user may interactively manipulate the spatial relationship of the plane or volume of interest relative to the volume dataset, using the needle, or by controlling a knob, mouse, joystick. etc.

In some embodiments, the thin depth-of-field volume can be displayed such that it is superimposed and spatially registered with organ/blood vessel/tumor surfaces or contours, radiation dose iso-contours, needle guidance information, or any other combination of relevant known polygonal or volumetric 3D data.

In some embodiments, when used with stereoscopic monitors, thin depth-of-field rendering can also be used to reduce ghosting (an undesired cross-talk between the two separate images for each eye. For example, a high-contrast line in the left-eye image may be slightly visible in the right-eye image). When used to reduce ghosting, the volume or plane of interest may be co-incident or nearly co-incident with the screen plane in 3D space (e.g., the surface of the display monitor).

In some embodiments, the volumetric data is sliced (e.g., resampled) into a set of image planes or image volumes that are parallel to the plane of interest. The distance between the image planes or volumes may be dependent on the resolution of the volume dataset, the display monitor's resolution, and the computational resources available (e.g., larger spacing may result in faster rendering and a higher frame rate, but a lower fidelity image in each frame). For example, an image plane (or volume) may be created for each depth resolution in the volumetric data, or a predefined or determined number of slices may be used. Each image plane or volume is then blurred; the "radius" of the blur may increase with the distance from the image slice to the plane or volume of interest (e.g., images slices further from the plane of interest may be made blurrier than image slices close to the plane-of-interest). The image plane coincident with the plane-of-interest itself may have no blur (e.g., it may be rendered using the standard reconstruction for the display monitor's resolution). In some embodiments, the image planes' brightness, contrast and/or transparency may then be modulated by their distance from the plane or volume of interest. In some embodiments, the planes may then be rendered in back-to-front order. Various embodiments may also be implemented directly on programmable graphics hardware, dedicated hardware, etc. to reduce processing time and/or memory usage.

In some embodiments, in order to reduce computational and memory demands, the image planes may be spaced such that the further they are from the plane-of-interest, the larger the distance between them. Those portions of the volume dataset that are farther away from the plane-of-interest, and thus displayed as blurrier and more transparent, will have a lower density of image-planes that sample them.

Tracking and Calibration

Image guidance systems provide real-time guidance to a medical practitioner during medical procedures. Numerous examples and embodiments of this are given herein. Image guidance systems require tracking. In order to track, there is typically a tracking "source" and a tracking "receiver," although there are many other arrangements known to those skilled in the art and discussed herein. Examples of tracking are discussed throughout herein and with respect to instruments 345 and 355 and tracking systems 310 and 340 in FIGS. 3A and 3B.

In order to track a device, some portion of the tracking system must be attached to the device. In some instances this may actually be a source, receiver, fiducial, etc. In optical tracking, for example, a tracking device is employed by the system to continually report the position and/or orientation of tracking fiducials that are attached to the devices to be tracked. In some embodiments, these fiducials are rigidly affixed to the needle or to its handle. With knowledge of the geometry of the needle, relative to the fiducials, an image guidance system can compute the position of the needle and its tip.

As noted above, each time a medical practitioner uses a new needle with a guidance system, she must rigidly affix the tracking fiducials to the needle and she must measure the position of the tip of the needle, relative to the fiducials. This is an extremely time consuming process. She must first tighten screws, or to thread the needle through a hole or tube. Then she must manually measure the needle length with a ruler (because needle lengths may vary even for standard needles), and then enter this information into a workstation. She may also be able to use a dedicated calibration rig, and perform a lengthy, often minutes-long calibration process. The same process occurs for other types of tracking systems as well.

Simplifying Calibration

Figure 20:
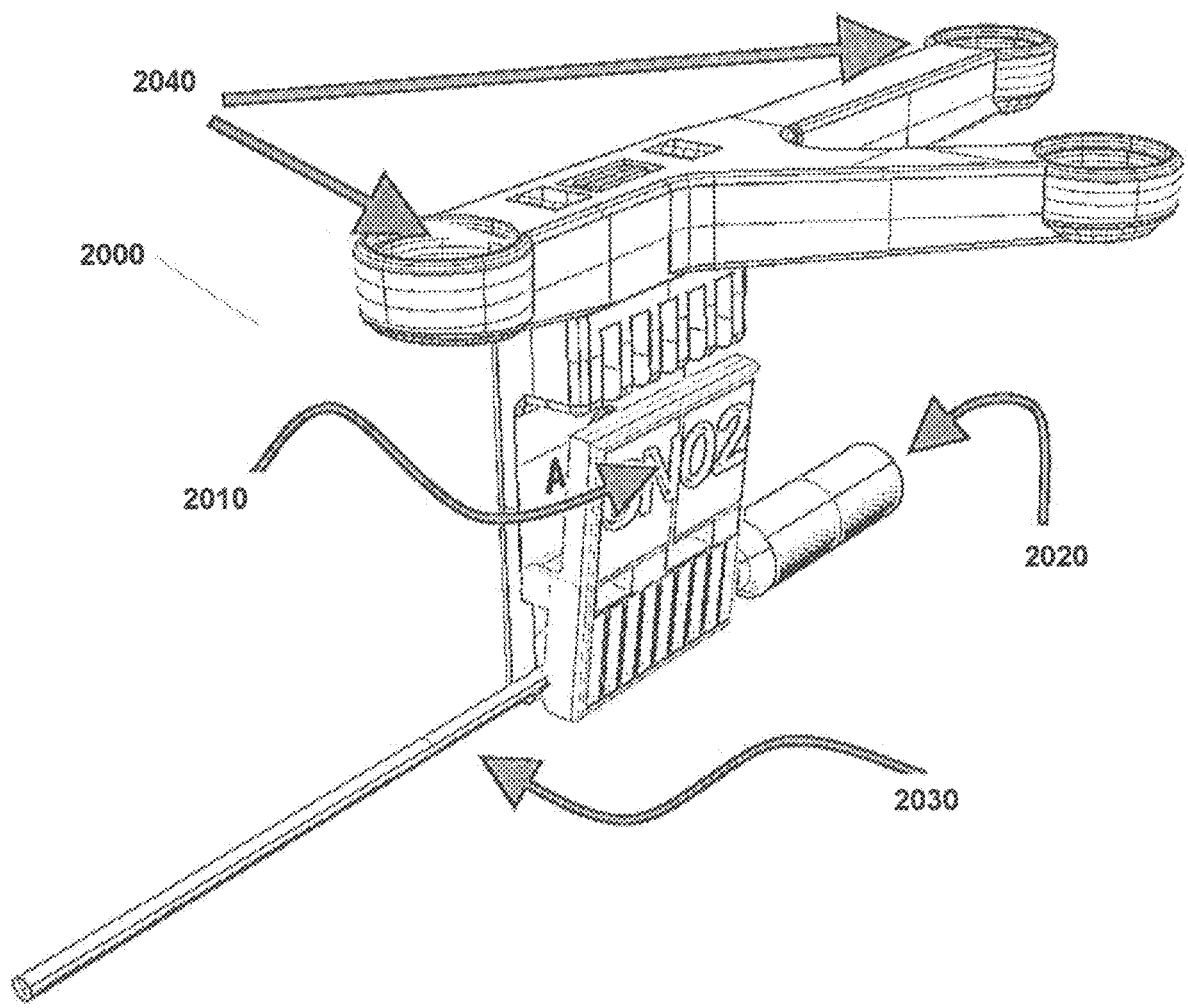
FIG. 20 illustrates a first calibration device for image guided surgery.

In order to simplify the calibration process, in some embodiments, the image guidance systems can utilize something that will indicate the needle's tip relative to a known or determinable location. If the needle is being tracked (even if not calibrated) when this is done, then the needle's tip relative to its own tracking fiducials can be calculated. For example, consider a needle's fiducial mount 2000 comprising a spring-loaded plastic clip 2010, with a groove embedded in the inner surfaces of both of the inner sides of the clip. In some embodiments, the tracking fiducials 2040 may be attached to a fixed piece of the clamp. The user may attach the needle by first pressing onto the side opposite the fulcrum to open the "jaws" (as depicted in FIG. 20). She may then insert the needle 2020 into the groove on the fixed part of the clamp while maintaining pressure upon the upper sides, above the pivot point, of the jaw with her thumb; she can then release her thumb. In some embodiments, she may perform this maneuver such that the distal end of the needle's shaft 2030 is flush with one end of the clip 2010. The spring may force the jaws 2010 to grip the needle shaft 2030, rather than being secured by a screw. In some embodiments, this design accommodates needles of varying shaft diameters. Also, in various embodiments, the needle 2020 is inserted by moving in a direction roughly perpendicular to its shaft axis and this may create a situation in which the tip of the needle does not come close to the jaws. This may reduce the chance of damage to the needle tip from the jaws, and further, allow mount to be removed even if the needle is still embedded in tissues.

In some embodiments, the spring action may be from a metal or other ancillary spring between the plastic. In some embodiments, the spring may be a coil or bent wedge design. In some embodiments, an integrated plastic or native material spring may also be incorporated into the molded parts. In some embodiments, the clamp components may be both molded, machined, or a combination thereof. In some embodiments, the materials may be medical grade plastic, which may provide light weight. The material may also be stainless steel, which may provide for easier or more economically sterilization. The apparatus can be made of any combination of plastic, metal, and ceramic, and can be fabricated by machining, casting, molding, or rapid prototyping (SLA, SLS, FDM, EBM, etc.). Further, in various embodiments, the needle may vibrate or heat up and the design of the needle mount's jaw accommodates this.

Figure 21:
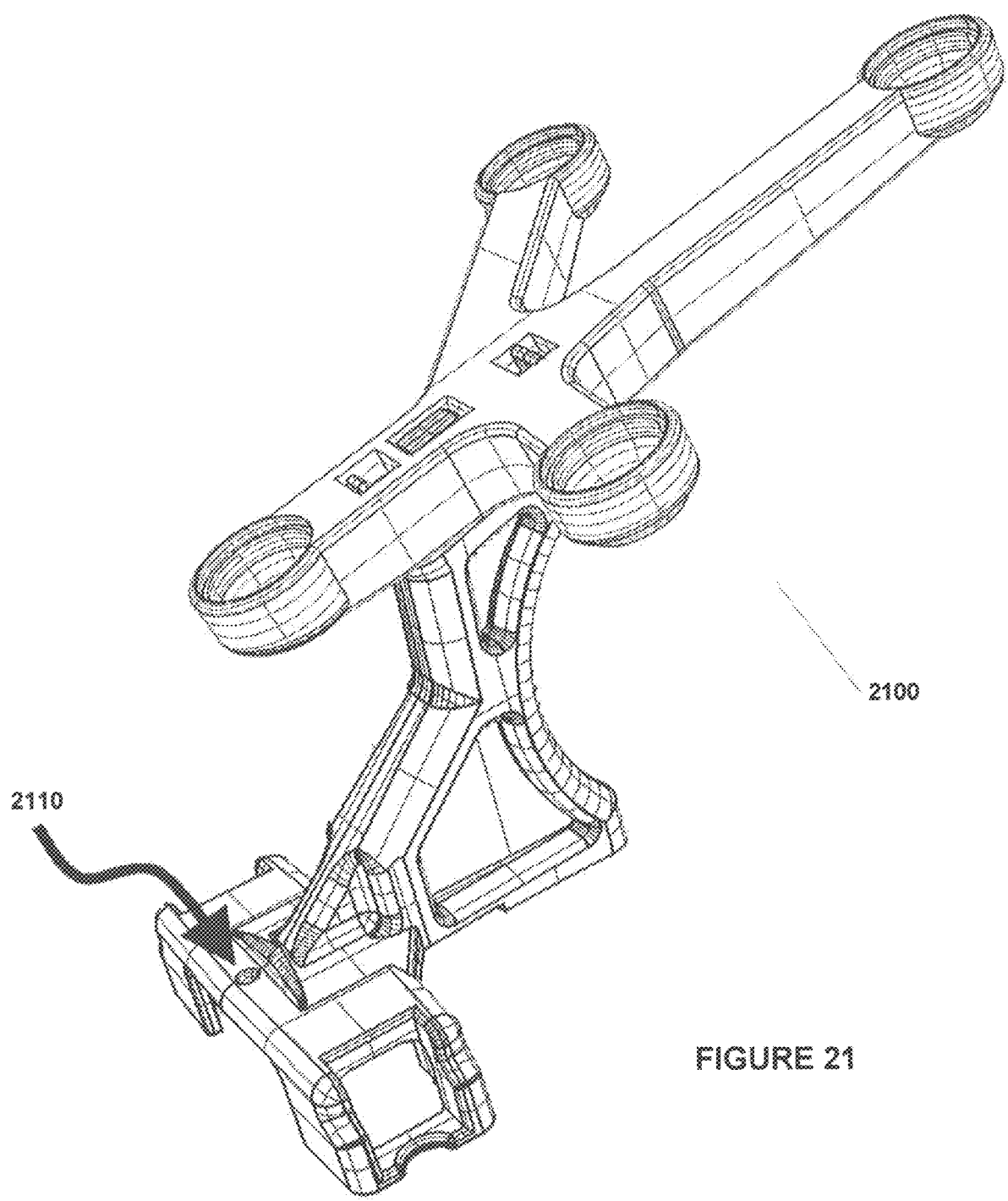
FIG. 21 illustrates a second calibration device for image guided surgery.
Figure 22:
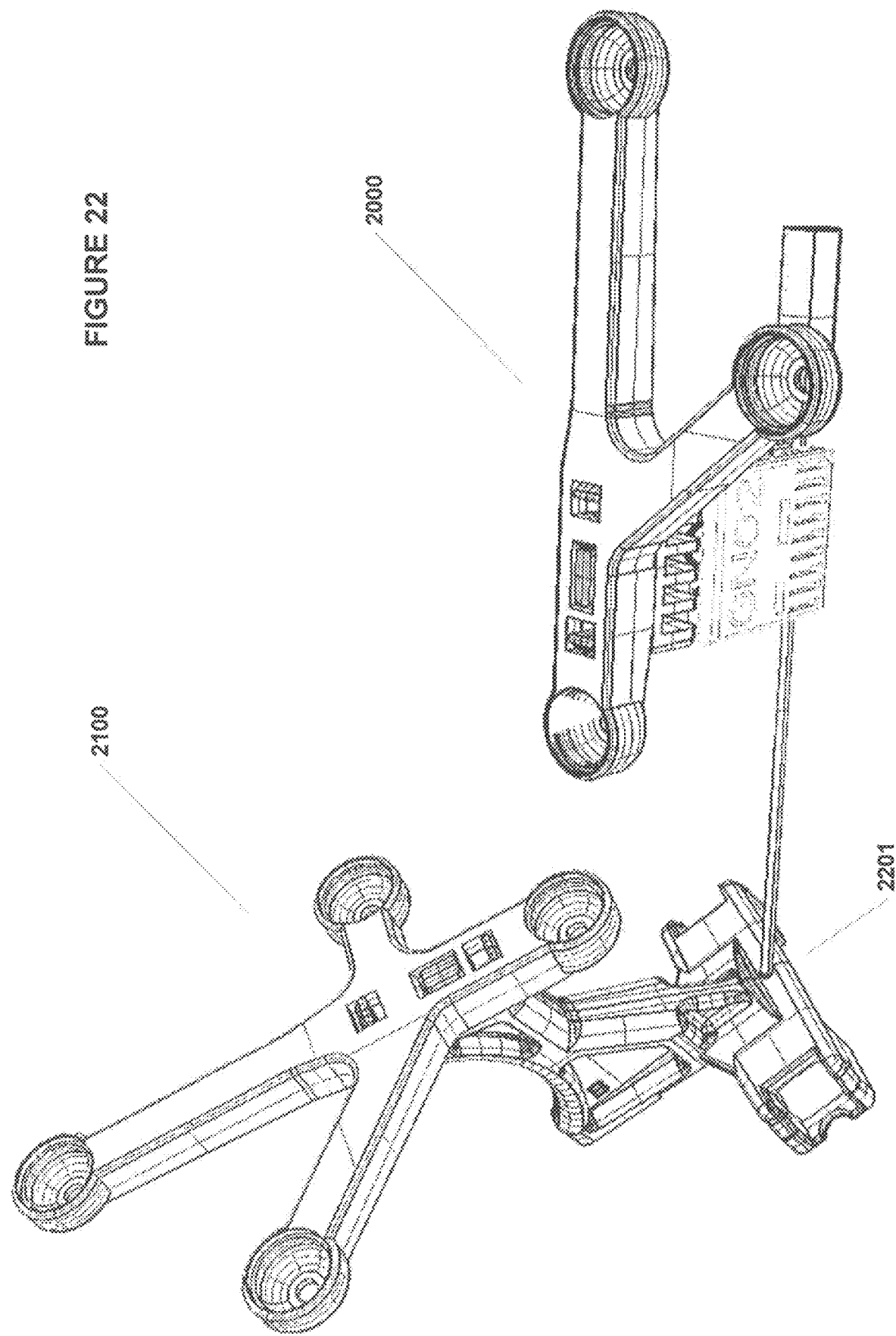
FIG. 22 illustrates an example of calibrating devices for image guided surgery.

A second tracked device, rig, or mount 2100 of FIG. 21 may provide the frame or reference. This tracked device 2100 may be something that is dedicated for this purpose, or it may be a tracked surgical device 2100 that is appropriately configured. For example, an ultrasound transducer may also be tracked. In some embodiments, the ultrasound transducer's tracking (fiducial) mount has divot, groove, etc. 2110 in it for receiving the needle tip. This is depicted in FIG. 21. The location of the divot relative to the ultrasound transducer's fiducials is known. Therefore, in some embodiments, by touching the needle tip to this divot as depicted in FIG. 22 at position 2201, the system can compute the needle tip's position relative to the fiducials attached to the needle.

Example embodiments of performing this calculation are as follows: The rigid body transformations listed below (which can be represented by 4×4 matrices, quaternions, etc.) may be known by the image guidance system:

transducerFiducials_from_tracker (the position and orientation of the ultrasound transducer's fiducials, relative to the tracking device's reference coordinate system)

needleFiducials_from_tracker (the position and orientation of the needle's fiducials, relative to the tracking device's reference coordinate system)

This position is also known: (which can be presented by a 4-element vector: {x,y,z,1}) divot_in_transducerFiducials (the position of the divot relative to the ultrasound transducer's fiducials)

In order to find needleTip_in_needleFiducials (the relative locations or transformation between the needle tip and the fiducials attached to the needles), various embodiments may perform the following calculations when the needle tip touches the divot:

needleTip_in_needleFiducials=divot_in_needleFiducials needleTip_in_needleFiducials=divot_in_tracker*tracker_from_needleFiducials needleTip_in_needleFiducials=divot_in_transducerFiducials*transducerFiducials_from_tracker*((needleFiducials_from_tracker)−1)

In some embodiments, the user may perform some or all of the following actions before the calculations above are performed:

1) The user may hold a needle tip in the divot and simultaneously presses a foot pedal to record their positions. As an alternative to a foot pedal, the user might ask her assistant to press a button (because the user herself cannot press the button as she has both hands occupied).

2) The user may hold down a foot pedal and hold the needle in the divot, then moves the transducer and needle together for roughly one second, while maintaining the needle in the divot, and then releases the foot pedal. This may results in more samples of positions and relative positions and may allow the system to more accurately determine (via regression, averaging, or other calculations) the position of the tip of the needle, relative to the needle fiducials.

Additionally, the image guidance system may be able to detect when the needle is in the divot by a gesture, voice command, duration in a single position, or any other appropriate method.

Various embodiments of these techniques may be used by any kind of medical professional—veterinarian, physician, surgeon, emergency medical technician, physician's assistant, nurse, etc. Various embodiments use different kinds of rigid needles, needle-like devices (e.g. radiofrequency or microwave ablation probe, cryo-ablation probe, cannula, optical waveguide, harmonic dissector, etc.). Various embodiments provide for the relative locations of a scalpel (where the divot may be replaced by a notched grove in order to locate the position of the scalpel, its tip, etc).

Various embodiments of tracking the various devices, such as devices 2100 and 2000, are discussed throughout herein and with respect to position sensing units 310 and 340 of FIGS. 3A and 3B. If optical tracking is used and the tracking system measures only the position of each fiducial, then three of more such fiducials may be affixed to the needle in order to compute the orientation of the needle. Otherwise, fewer than three fiducials may be attached.

Rendering Techniques

Asynchronous Rendering

As noted above, real-time, live, or intraoperative data may be used and rendered in various embodiments herein. The update rate of the various data used may differ, and some may be slow enough, that if the entire image were only updated at that rate, a physician may be able to notice the update, which may be undesirable. For example, if an ultrasound were only updated once per second and the entire scene were only rendered once per second, the physician is likely to notice this and find the system unusable. Perceivable lag can increase the risk of simulator sickness, and the system might appear unresponsive. In various embodiments, the 3D display herein is designed to reduce response time and may appear to match the physician's movements with less or no perceivable lag. To accomplish this, various embodiments use asynchronous rendering. In some embodiments, no process or operation in a thread that renders the video or screen images waits for new data from the data from the other devices or systems, such as the tracking system or ultrasound scanner. Instead those threads use the latest available data. In some embodiments, two accessory threads query the tracker (such as position sensing units 310 and 340 in FIGS. 3A and 3B) and a video frame grabber, which may be part of an image guidance system such as image guidance system 300 of FIGS. 3A and 3B. These threads wait as their respective hardware delivers the requested data, and then update the main thread's relevant data structures as soon as they have new data, without causing the main thread to wait. Therefore, the main or graphical rendering thread can continue to update the image with whatever data is available for the tracking, imaging, and other data.

Similarly, the image guidance unit's main thread may instruct associated graphics hardware to swap the front and back display buffers immediately after drawing a new image in the back buffer, without waiting for the vertical sync signal. This allows the newly drawn graphics to appear on the display monitor sooner, and may allow for a higher graphics frame rate. Using this asynchronous technique a user might notice tearing in both the ultrasound image and in the graphics display. However, in some embodiments, the image guidance system grabs video frames much faster than an imager, such as an ultrasound scanner generates frames. The image guidance system may also draw frames much faster than the refresh rate of the LCD display monitor. As such, any tearing between successive frames will be evenly distributed, and may be less noticeable to the human eye. At a 60 Hz video refresh rate, we would expect that 17 ms (1/60 Hz) of latency may be avoided by not waiting for vertical sync. In some embodiments, latency may be reduced by up to 70 ms (or more).

These techniques may allow for low latency without requiring the various sub-systems to necessarily be tuned to each other or wait for each other.

Other Exemplary Embodiments For Various Procedures

Removal of Fibroids

In some embodiments, the image guidance system may be used to remove fibroids, while leaving the uterine muscle wall strong enough to carry a fetus. For example, when a physician finds a fibroid with a tracked laparoscopic ultrasound, the image guidance system, such as system 300 of FIGS. 3A and 3B, may display a visualization of a dissection tool relative to the fibroid in the ultrasound image. This may help the physician cut the muscle wall down the midline of the fibroid, or other desired cut approach. Such embodiments may reduce the damage the muscle wall, which may then be more likely to support pregnancy. These embodiments may also reduce the amount of stitching, and reduce the time to remove a fibroid.

In some embodiments, the system may be configured to allow for ablation of fibroids. For example, system 300 of FIGS. 3A and 3B may include a tracked ablation antenna 345 and a tracked external ultrasound probe 355, laparoscopic ultrasound transducer 355, etc. The image guidance unit 330 may provide guidance information on the display 320, e.g., including the relative positions or emplacements of the fibroid in the ultrasound image and the tip, projection, and/or expected ablation volume of the ablation needle 345. This guidance information may allow the physician to more quickly locate and place the ablation needle into fibroids.

Today, surgeons often target fibroids 3-4 cm wide. In some embodiments, a surgeon may be able to find smaller fibroids (such as those 1 cm wide and smaller) because of the accuracy of the tracking and imaging, thereby increasing the probably of the patient carrying a baby to term, and decreasing other symptoms resulting from fibroids.

Ablation of Pancreatic Cysts

Pancreatic cysts may be a precursor to pancreatic cancer. Therefore, it may be useful to ablate the pancreatic cysts when they occur, whether or not it is certain that pancreatic cancer would necessarily follow.

In some embodiments, the image guidance system may be used aid a physician in ablating the pancreatic cysts. For example, in some embodiments, an image guidance system, such as the system 300 of FIGS. 3A and 3B may include an endoscopic ultrasound transducer 355 and an ablator 345, such as an ablation needle 345. In some embodiments, the ablator uses laser light, microwave, radio wave, or any other appropriate ablation energy or technique. In some embodiments, the ultrasound transducer is inserted via the mouth and images the pancreas through the wall of stomach or duodenum, while the ablation needle enters the patient from outside the body.

Hysteroscopy

Some physicians remove fibroids using a hysteroscope, or other flexible endoscope that passes through the vagina and cervix and functions inside the uterus. Hysteroscopy may be less invasive that other forms of laparoscopic surgery because of the lack of incision and insufflation. Further, hysteroscopy can sometimes be performed in a clinic instead of a hospital, thereby potentially reducing costs.

In some embodiments, a hysteroscope is tracked and imaged by an image guidance system, such as system 300 of FIGS. 3A and 3B. In order to image fibroids, a physician may use external ultrasound, filling the bladder with water so that she can image through it and see the uterus. In some embodiments, a resectoscope, which may be a hysteroscope with a wire loop extending from it, may be used by the physician and with an embodiment of the image guidance system. The resectoscope may have a semi-circular loop in a plane parallel to the image plane that can translate forward and back (toward and away from the lens). The wire loop may be energized (e.g., electrocauterizer) and carve away a detected fibroid. In some embodiments, the image guidance system may track the resectoscope or hysteroscope and render the resector wire loop, relative to the ultrasound scan or any other devices used.

Harvesting Eggs

In some embodiments, the image guidance system is used to track and visualize the ultrasound data as well as the needle that is used to collect the eggs from the ovary. For example, in order to harvest eggs a transvaginal ultrasound probe to visualize the follicles in the ovary, which may contain eggs, may be used. The image guidance may help the physician get a flexible needle (16 gauge, 30 cm long) into each follicle, through the vaginal wall. A physician may push on the outside of the patient to push the ovary into a position where it can be imaged and accessed through the vaginal wall. Each follicle containing an egg is typically 1-2 cm wide. The physician may drain (aspirate) the contents of the follicle, and then examine the fluid to look for an egg. The physician may then proceed to the next follicle. She may collect 9-10 eggs, or even more. Eggs are often attached to the side of the follicle, and the needle should enter the center of the follicle in order to safely remove it from the wall. Embodiments herein make that targeting easier by tracking the needle and the ultrasound (or other imaging) that is used to find the eggs. Such embodiments used for this procedure may be a more effective procedure than is currently available.

Embryo Attachment

In some embodiments, the image guidance system is used for embryo attachment or embryo transfer. Embryos are inserted via a flexible catheter through the cervix. The catheter consists of a flexible inner tube within a more rigid external tube, each about 10-20 cm long. While the inner tube may be very flexible, the outer tube may be stiffer and allows a physician to guide the inner tube. The physician may fill the bladder with water, and uses external ultrasound to image the uterus through the bladder. The ideal place to implant the embryos is the "maximal implantation potential (MIP) point", which is roughly the "top" of the uterus, between the fallopian tubes. A surgeon may use ultrasound to find this point (possibly marking the point as discussed herein), and guide the catheter there. The goal is to implant between the two layers of the uterine lining, but "it's hard to see where the tip goes" once it is inside the uterine lining.

The catheter and/or the tip of the inner tube may be tracked and its emplacement relative to the ultrasound image may be displayed to the physician via the image guidance system. For example, the tip of the catheter may be tracked and its real-time emplacement shown relative to the ultrasound image or marked MIP. In some embodiments, in addition to tracking the very tip of the inner catheter, the image guidance system also tracks one or more points along the catheter. As such, the image guidance system can display the catheter's shape near its tip.

If a physician can get the embryo into the right place, it may increase the overall success rate. This, in turn, could eventually allow physicians to implant fewer embryos, perhaps reducing the "twin rate."

The processes, computer readable medium, and systems described herein may be performed on various types of hardware, such as computer systems. In computer systems may include a bus or other communication mechanism for communicating information, and a processor coupled with the bus for processing information. A computer system may have a main memory, such as a random access memory or other dynamic storage device, coupled to the bus. The main memory may be used to store instructions and temporary variables. The computer system may also include a read-only memory or other static storage device coupled to the bus for storing static information and instructions. The computer system may also be coupled to a display, such as a CRT or LCD monitor. Input devices may also be coupled to the computer system. These input devices may include a mouse, a trackball, or cursor direction keys. Computer systems described herein may include the image guidance unit 330, first and second position sensing units 310 and 340, and imaging unit 350. Each computer system may be implemented using one or more physical computers or computer systems or portions thereof. The instructions executed by the computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A method for medical device navigation, the method comprising:
   receiving real-time medical imaging data;
   determining an emplacement of a 2D medical image based at least in part on the real-time medical imaging data and emplacement data associated with a first physical medical device;
   determining an emplacement of a virtual medical device based at least in part on emplacement data associated with a second physical medical device;
   determining an intersection between an axis of the virtual medical device and the 2D medical image based at least in part on the emplacement of the 2D medical image and the emplacement of the virtual medical device; and
   causing one or more displays to concurrently display, in a virtual 3D space:
      a perspective view of the 2D medical image based at least in part on a relative orientation of the first physical medical device with respect to an expected location of a user, and
      an indication of the intersection between the axis of the medical device and the 2D medical image.

2. The method of claim 1, further comprising:
determining a distance between a tip of the virtual medical device and a point on the 2D medical image that is closest to the tip of the virtual medical device; and
causing the one or more displays to further concurrently display:
an indication of the distance.

3. The method of claim 1, wherein the second physical medical device comprises an ablation needle, wherein the method further comprises:
determining an emplacement of an ablation volume based at least in part on the emplacement data associated with the second physical medical device;
determining a portion of the ablation volume that intersects with the 2D medical image; and
causing the one or more displays to further concurrently display:
an indication of the portion of the ablation volume that that intersects with the 2D medical image, wherein the indication of the portion of the ablation volume is coplanar with the 2D medical image.

4. The method of claim 1, further comprising causing the one or more displays to display a perspective view of the virtual medical device based at least in part on a relative orientation of the second physical medical device with respect to the expected location of the user.

5. The method of claim 1, further comprising:
determining a perspective view of the 2D medical image based at least in part on a relative orientation of the first physical medical device with respect to a particular location,
wherein said causing the one or more displays to concurrently display the 2D medical image comprising causing the one or more displays to concurrently display the perspective view of the 2D medical image.

6. The method of claim 5, wherein the expected location of the user is a fixed location in front of the one or more displays.

7. A method for image guidance comprising:
receiving real-time medical imaging data;
determining an emplacement of a medical image based at least in part on the real-time medical imaging data and emplacement data associated with a physical medical device; and
causing one or more displays to concurrently display, in a virtual 3D space, a perspective view of at least a portion of the medical image, wherein the perspective view is based at least in part on a relative emplacement of the physical medical device with respect to an expected location of a user.

8. The method of claim 7, wherein the expected location comprises a location from which the one or more displays are visible.

9. The method of claim 7, wherein the expected location of the user is a fixed location in front of the one or more displays.

10. The method of claim 7, wherein said causing the one or more displays to display the perspective view comprises causing the one or more displays to display the perspective view in real-time.

11. The method of claim 7, wherein the physical medical device comprises an imaging device.

12. The method of claim 7, further comprising causing the one or more displays to display a graphic indicating an intersection between a trajectory of a virtual medical device and a location on a 2D plane corresponding to the medical image.

13. The method of claim 7, wherein the physical medical device is a first physical medical device, the method further comprising:
determining an emplacement of a virtual medical device based at least in part on emplacement data associated with a second physical medical device; and
causing the one or more displays to display in real-time a perspective view of an ablation volume corresponding to the virtual medical device based at least in part on the emplacement of the virtual medical device.

14. A system for image guidance comprising one or more processors configured to:
receive real-time medical imaging data;
determine an emplacement of a medical image based at least in part on the real-time medical imaging data and emplacement data associated with a medical imaging device; and
cause one or more displays to display, in a virtual 3D space, a perspective view of at least a portion of the medical image, wherein the perspective view is based at least in part on a relative emplacement of the medical imaging device with respect to an expected location of a user.

15. The system of claim 14, wherein the expected location comprises a location from which the one or more displays are visible.

16. The system of claim 14, wherein the expected location of the user is a fixed location in front of the one or more displays.

17. The system of claim 14, wherein the one or more processors are further configured to cause the one or more displays to display a graphic indicating an intersection between a trajectory of a virtual medical device and a location on a 2D plane corresponding to the medical image.

18. The system of claim 14, wherein the one or more processors are further configured to:
determine an emplacement of a physical medical device based at least in part on emplacement data associated with a physical medical device; and
cause the one or more displays to display in real-time an ablation volume corresponding to the physical medical device based at least in part on the emplacement of the physical medical device.

* * * * *